United States Patent [19]
Stevens et al.

[11] Patent Number: 6,029,671
[45] Date of Patent: Feb. 29, 2000

[54] SYSTEM AND METHODS FOR PERFORMING ENDOVASCULAR PROCEDURES

[75] Inventors: John H. Stevens, Palo Alto; William S. Peters, Woodside; Wesley D. Sterman, San Francisco; Hanson S. Gifford, III, Woodside, all of Calif.

[73] Assignee: Heartport, Inc., Redwood City, Calif.

[21] Appl. No.: 08/650,112

[22] Filed: May 22, 1996

Related U.S. Application Data

[60] Division of application No. 08/415,366, Mar. 30, 1995, abandoned, and a continuation-in-part of application No. 08/282,192, Jul. 28, 1994, Pat. No. 5,584,803, which is a continuation-in-part of application No. 08/162,742, Dec. 3, 1993, abandoned, which is a continuation-in-part of application No. 08/123,411, Sep. 17, 1993, abandoned, which is a continuation-in-part of application No. 07/991,188, Dec. 15, 1992, abandoned, which is a continuation-in-part of application No. 07/730,559, Jul. 16, 1991, Pat. No. 5,370,685, application No. 08/159,815, Nov. 30, 1993, Pat. No. 5,433,700, and application No. 08/281,962, Jul. 28, 1994, abandoned, which is a continuation-in-part of application No. 08/163,241, Dec. 6, 1993, Pat. No. 5,571,215, which is a continuation-in-part of application No. 08/023,778, Feb. 22, 1993, Pat. No. 5,452,733, and application No. 08/281,891, Jul. 28, 1994, Pat. No. 5,735,290, which is a continuation-in-part of application No. 08/023,778, Feb. 22, 1993, Pat. No. 5,452,733.

[51] Int. Cl.[7] .................................................. A61B 19/00
[52] U.S. Cl. .................................. 128/898; 606/194
[58] Field of Search ........................... 604/96, 103, 110, 604/418, 113, 30, 35, 415, 4–8, 109; 128/898; 600/18, 36; 606/192, 194, 159, 45, 167–72; 623/2, 900

[56] References Cited

U.S. PATENT DOCUMENTS

| | | |
|---|---|---|
| Re. 33,569 | 4/1991 | Gifford, III et al. . |
| 3,730,185 | 5/1973 | Cook et al. . |

(List continued on next page.)

FOREIGN PATENT DOCUMENTS

| | | |
|---|---|---|
| 0 218 275 | 8/1986 | European Pat. Off. . |
| WO 94/16625 | 8/1994 | WIPO . |

OTHER PUBLICATIONS

Okita et al., "Utilization of Triple–Lumen Balloon Catheter for Occlusion of the Ascending Aorta During Distal Aortic Arch Surgery with Hypothermic Retrograde Cerebral Circulation Technique Through Left Thoracotomy," *J Card Surg*, 1995; 10:699–702.

*Primary Examiner*—Mickey Yu
*Assistant Examiner*—Kelly O'Hara
*Attorney, Agent, or Firm*—Jens E. Hoekendijk; Jeffry J. Grainger

[57] ABSTRACT

A system for inducing cardioplegic arrest and performing an endovascular procedure within the heart or blood vessels of a patient. An endoaortic partitioning catheter has an inflatable balloon which occludes the ascending aorta when inflated. Cardioplegic fluid may be infused through a lumen of the endoaortic partitioning catheter to stop the heart while the patient's circulatory system is supported on cardiopulmonary bypass. One or more endovascular devices are introduced through an internal lumen of the endoaortic partitioning catheter to perform a diagnostic or therapeutic endovascular procedure within the heart or blood vessels of the patient. Surgical procedures such as coronary artery bypass surgery or heart valve replacement may be performed in conjunction with the endovascular procedure while the heart is stopped. Embodiments of the system are described for performing: fiberoptic angioscopy of structures within the heart and its blood vessels, valvuloplasty for correction of valvular stenosis in the aortic or mitral valve of the heart, angioplasty for therapeutic dilatation of coronary artery stenoses, coronary stenting for dilatation and stenting of coronary artery stenoses, atherectomy or endarterectomy for removal of atheromatous material from within coronary artery stenoses, intravascular ultrasonic imaging for observation of structures and diagnosis of disease conditions within the heart and its associated blood vessels, fiberoptic laser angioplasty for removal of atheromatous material from within coronary artery stenoses, transmyocardial revascularization using a side-firing fiberoptic laser catheter from within the chambers of the heart, and electrophysiological mapping and ablation for diagnosing and treating electrophysiological conditions of the heart.

1 Claim, 14 Drawing Sheets

U.S. PATENT DOCUMENTS

| | | |
|---|---|---|
| 4,195,637 | 4/1980 | Gruntzig et al. . |
| 4,273,128 | 6/1981 | Lary . |
| 4,290,427 | 9/1981 | Chin . |
| 4,315,511 | 2/1982 | Chin . |
| 4,323,071 | 4/1982 | Simpson et al. . |
| 4,490,421 | 12/1984 | Levy . |
| 4,522,212 | 6/1985 | Gelinas et al. . |
| 3,874,388 | 4/1975 | King et al. . |
| 4,000,739 | 1/1977 | Stevens . |
| 4,538,622 | 9/1985 | Samson et al. . |
| 4,545,390 | 10/1985 | Leary . |
| 4,574,781 | 3/1986 | Chin . |
| 4,589,412 | 5/1986 | Kensey . |
| 4,616,653 | 10/1986 | Samson et al. . |
| 4,621,636 | 11/1986 | Fogarty . |
| 4,660,571 | 4/1987 | Hess et al. . |
| 4,664,120 | 5/1987 | Hess . |
| 4,669,469 | 6/1987 | Gifford, III et al. . |
| 4,699,147 | 10/1987 | Chilson et al. . |
| 4,740,047 | 4/1988 | Abe et al. . |
| 4,748,982 | 6/1988 | Horzewski et al. . |
| 4,762,129 | 8/1988 | Bonzel . |
| 4,771,774 | 9/1988 | Simpson et al. . |
| 4,781,186 | 11/1988 | Simpson et al. . |
| 4,787,388 | 11/1988 | Hofmann . |
| 4,788,975 | 12/1988 | Shturman et al. . |
| 4,794,931 | 1/1989 | Yock . |
| 4,796,629 | 1/1989 | Grayzel . |
| 4,854,325 | 8/1989 | Stevens . |
| 4,856,516 | 8/1989 | Hillstead . |
| 4,874,089 | 10/1989 | Matsuda et al. . |
| 4,883,460 | 11/1989 | Zanetti . |
| 4,890,611 | 1/1990 | Monfort et al. . |
| 4,909,252 | 3/1990 | Goldberger . |
| 4,917,089 | 4/1990 | Sideris . |
| 4,917,097 | 4/1990 | Proudian et al. . |
| 4,924,863 | 5/1990 | Sterzer . |
| 4,960,134 | 10/1990 | Webster, Jr. . |
| 4,976,690 | 12/1990 | Solar et al. . |
| 4,988,356 | 1/1991 | Crittenden et al. . |
| 5,000,185 | 3/1991 | Yock . |
| 5,000,743 | 3/1991 | Patel ........................................ 606/194 |
| 5,011,469 | 4/1991 | Buckberg et al. ........................... 604/4 |
| 5,024,234 | 6/1991 | Leary et al. . |
| 5,026,366 | 6/1991 | Leckrone . |
| 5,029,588 | 7/1991 | Yock et al. . |
| 5,037,392 | 8/1991 | Hillstead . |
| 5,040,548 | 8/1991 | Yock . |
| 5,041,126 | 8/1991 | Gianturco . |
| 5,055,024 | 10/1991 | Jackowski et al. . |
| 5,061,273 | 10/1991 | Yock . |
| 5,071,424 | 12/1991 | Reger . |
| 5,071,425 | 12/1991 | Gifford, III et al. . |
| 5,104,393 | 4/1992 | Isner et al. . |
| 5,125,896 | 6/1992 | Hojeibane . |
| 5,140,987 | 8/1992 | Schuger et al. . |
| 5,147,353 | 9/1992 | Everett . |
| 5,156,610 | 10/1992 | Reger . |
| 5,163,935 | 11/1992 | Black et al. . |
| 5,167,233 | 12/1992 | Eberle et al. . |
| 5,178,625 | 1/1993 | Groshong . |
| 5,188,634 | 2/1993 | Hussein et al. . |
| 5,190,046 | 3/1993 | Shturman . |
| 5,195,956 | 3/1993 | Stockmeier . |
| 5,211,651 | 5/1993 | Reger et al. . |
| 5,242,437 | 9/1993 | Everett et al. . |
| 5,242,438 | 9/1993 | Saadatmanesh et al. . |
| 5,264,260 | 11/1993 | Saab . |
| 5,267,955 | 12/1993 | Hanson . |
| 5,282,484 | 2/1994 | Reger . |
| 5,295,958 | 3/1994 | Shturman . |
| 5,312,344 | 5/1994 | Grinfeld et al. . |
| 5,327,889 | 7/1994 | Imran . |
| 5,354,294 | 10/1994 | Chou . |
| 5,366,456 | 11/1994 | Rink et al. . |
| 5,368,037 | 11/1994 | Eberle et al. . |
| 5,368,603 | 11/1994 | Halliburton . |
| 5,380,316 | 1/1995 | Aita et al. . |
| 5,389,096 | 2/1995 | Aita et al. . |
| 5,433,700 | 7/1995 | Peters . |
| 5,451,207 | 9/1995 | Yock . |
| 5,456,694 | 10/1995 | Marin et al. . |
| 5,458,574 | 10/1995 | Machold et al. ........................ 604/101 |
| 5,478,309 | 12/1995 | Sweezer et al. . |

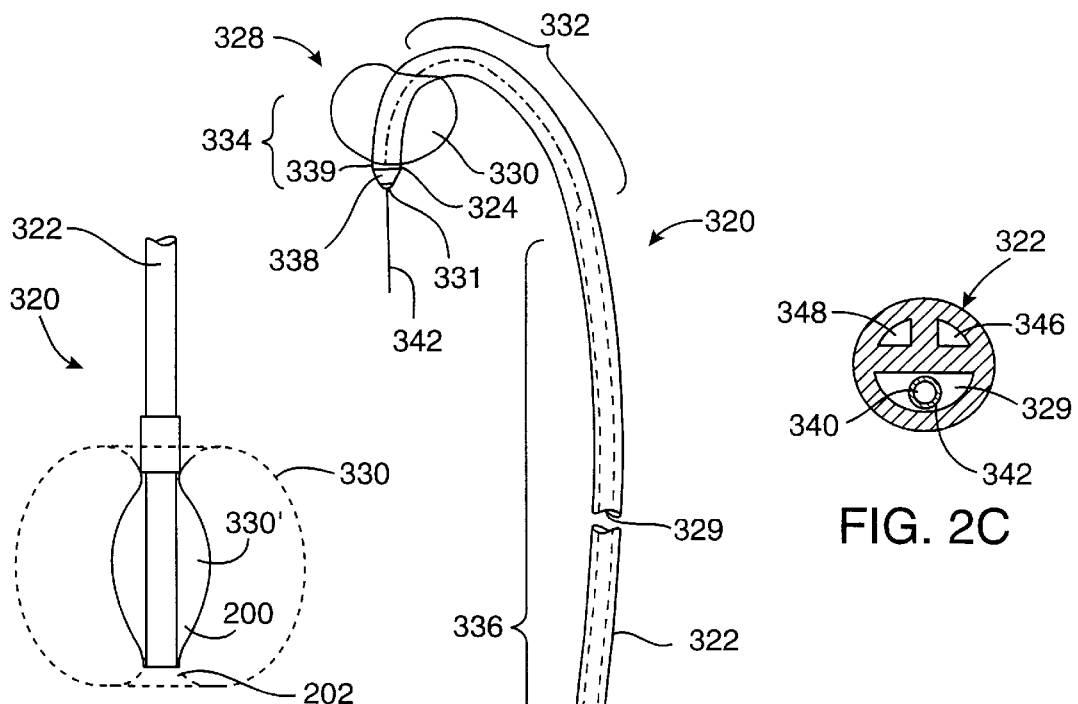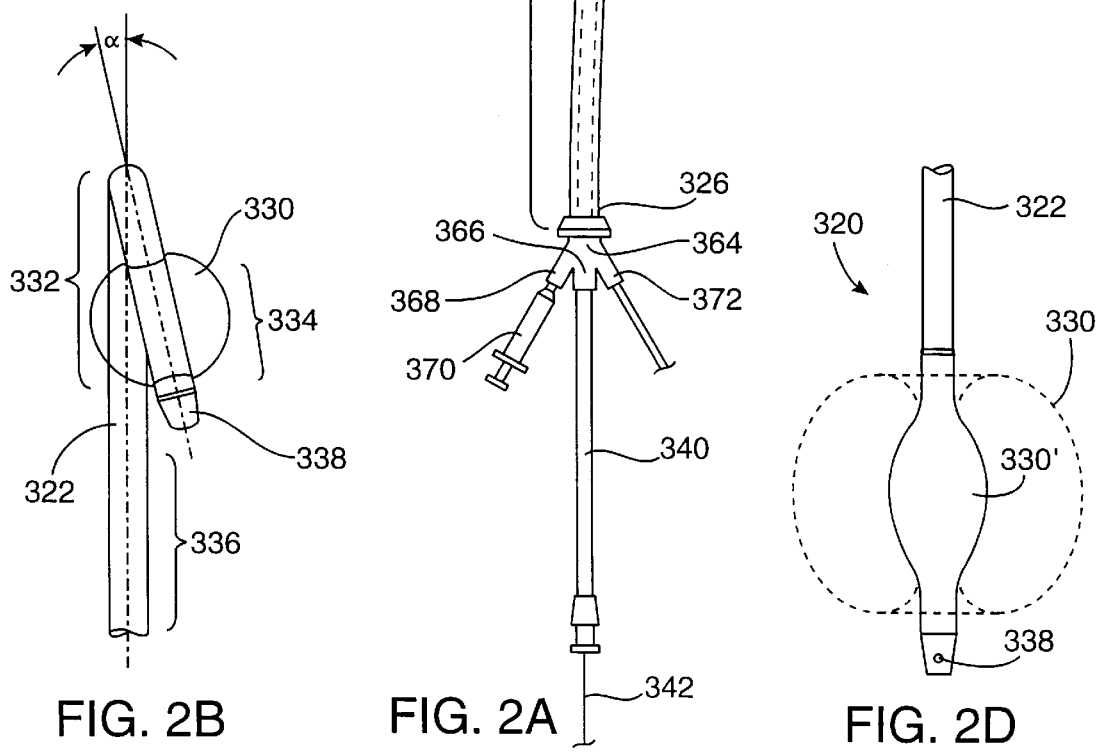

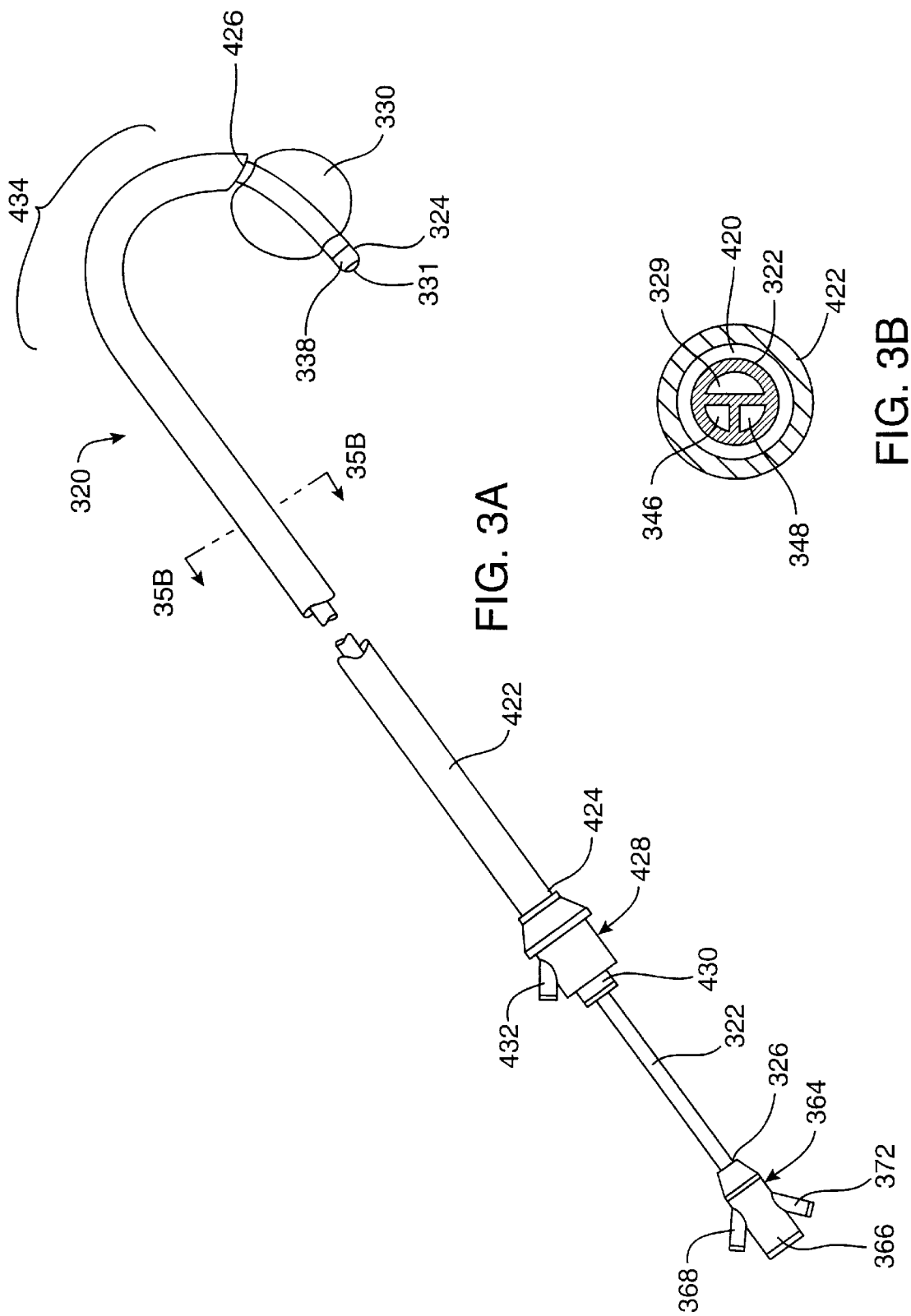

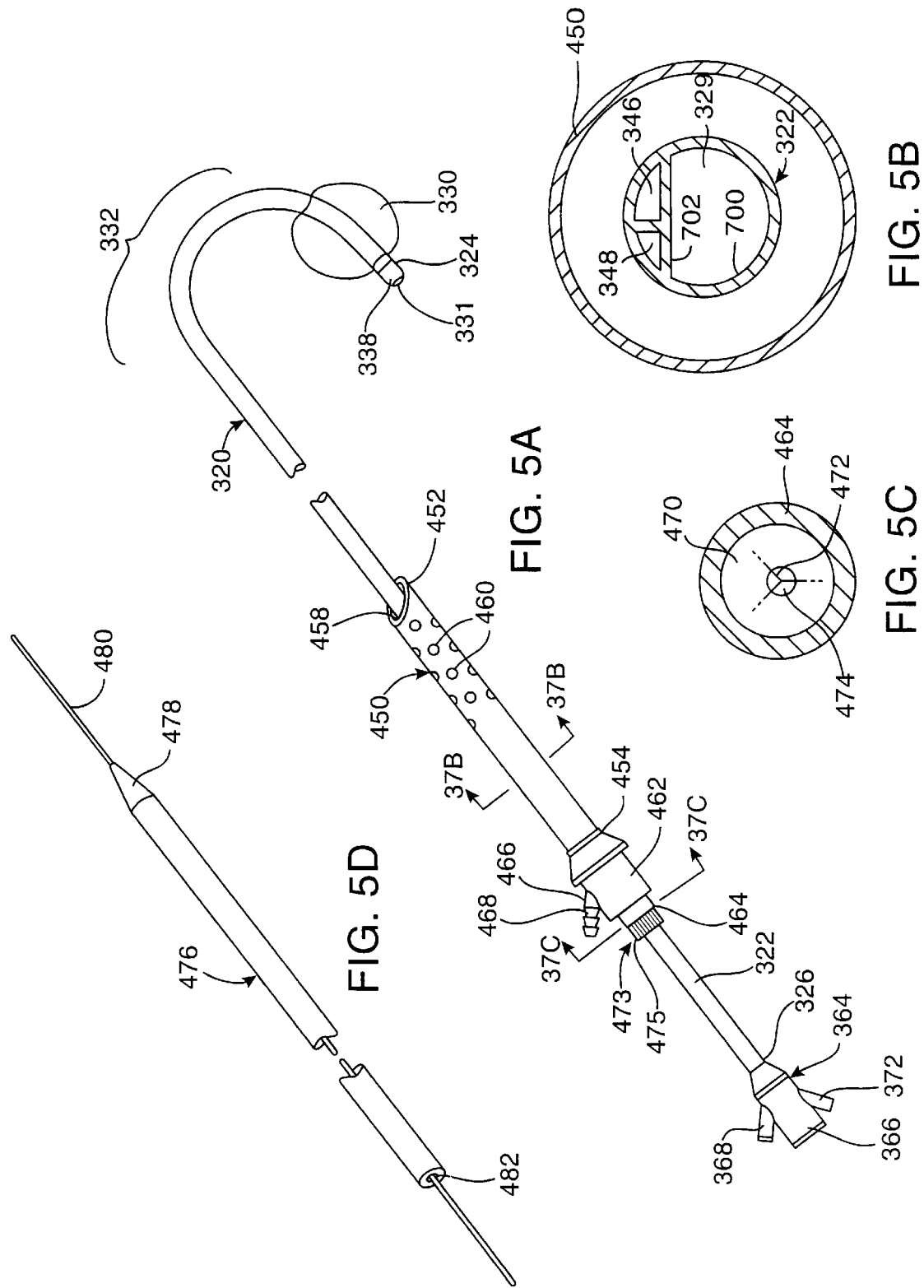

SYSTEM AND METHODS FOR PERFORMING ENDOVASCULAR PROCEDURES

CROSS-REFERENCE TO RELATED APPLICATIONS

This is a Division of application Ser. No. 08/415,366, filed Mar. 30, 1995, now abandoned, of JOHN H. STEVENS, WILLIAM S. PETERS, WESLEY D. STERMAN and HANSON S. GIFFORD, entitled "SYSTEM AND METHODS FOR PERFORMING ENDOVASCULAR PROCEDURES" and a continuation-in-part of application of U.S. patent application Ser. No. 08/282,192, filed Jul. 28, 1994 which issued as U.S. Pat. No. 5,584,803 on Dec. 17, 1996, and is a continuation-in-part of application Ser. No. 08/162,742, filed Dec. 3, 1993, now abandoned which is a continuation-in-part of application Ser. No. 08/123,411, filed Sep. 17, 1993, now abandoned which is a continuation-in-part of application Ser. No. 07/991,188, filed Dec. 15, 1992, now abandoned which is a continuation-in-part of application Ser. No. 07/730,559, filed Jul. 16, 1991, which issued as U.S. Pat. No. 5,370,685 on Dec. 6, 1994. This application is also a continuation-in-part of U.S. patent application Ser. No. 08/159,815, filed Nov. 30, 1993, which issued as U.S. Pat. No. 5,433,700 on Jul. 18, 1995, and was reissued as U.S. Pat. No. RE35,352 on Oct. 15, 1996 which is a U.S. counterpart of Australian Patent Application No. PL 6170, filed Dec. 3, 1992. This application is also a continuation-in-part of U.S. patent application Ser. No. 08/281, 962, filed Jul. 28, 1994, now abandoned which is a continuation-in-part of application Ser. No. 08/163,241, filed Dec. 6, 1993, which issued as U.S. Pat. No. 5,571,215 on Nov. 5, 1996, which is a continuation-in-part of application Ser. No. 08/023,778, filed Feb. 22, 1993 which issued as U.S. Pat. No. 5,452,733 on Sep. 26, 1995. This application is also a continuation-in-part of U.S. patent application Ser. No. 08/281,891, filed Jul. 28, 1994 now U.S. Pat. No. 5,735,290, which is a continuation-in-part of application Ser. No. 08/023,778, filed Feb. 22, 1993 which issued as U.S. Pat. No. 5,452,733 on Sep. 26, 1995. The complete disclosures of all of the forementioned related U.S. patent applications are hereby incorporated herein by reference for all purposes.

FIELD OF THE INVENTION

The present invention relates generally to devices and methods for performing diagnostic or therapeutic endovascular procedures within the circulatory system of a patient. More particularly, it relates to a system for isolating the heart and coronary blood vessels of a patient from the remainder of the arterial system, for inducing cardioplegic arrest in the heart and for performing diagnostic or therapeutic endovascular procedures within the heart or blood vessels of the patient while the heart is stopped.

BACKGROUND OF THE INVENTION

Recent trends in the advancement of surgical technology have tended toward less and less invasive procedures in order to reduce morbidity and mortality of the surgical procedures, thereby increasing the benefit to the patient.

An important advancement in the area of cardiac surgery is represented by co-owned, copending patent applications, Ser. Nos. 08/281,981 and 08/281,962, which describe, in detail, endoaortic catheter devices and systems for inducing cardioplegic arrest in the heart of a patient and for carrying out surgical procedures, such as coronary artery bypass graft (CABG) surgery or heart valve replacement surgery, on the arrested heart. One surgical approach presented in the parent applications is known as closed-chest or port-access cardiac surgery, in which access is gained to the exterior of the heart through percutaneous intercostal penetrations in the wall of the patient's chest. In port-access cardiac surgery the surgical procedure is carried out using instruments that operate through the intercostal penetrations while the heart is stopped using the endoaortic catheter. Another surgical approach presented in the parent applications is an endovascular approach, in which diagnostic or therapeutic endovascular devices are inserted through a lumen in the endoaortic catheter to carry out an endovascular procedure within the heart or blood vessels of the patient. The present invention addresses the endovascular surgical approach and the endovascular procedures that can be carried out using the endoaortic catheter.

It has been suggested previously to combine certain endovascular procedures as an adjunct to cardiac surgery procedures, such as combining intraoperative coronary balloon angioplasty with conventional coronary artery bypass grafting in order to achieve more complete revascularization of the patient's coronary arteries. To date there has only been very limited clinical acceptance of this combined procedure. One reason for this limited acceptance may be that the standard aortic crossclamps used for isolating the heart from the remainder of the arterial system during CABG surgery occlude the aortic lumen, preventing the angioplasty catheter from being introduced into the coronary arteries by the usual transluminal approach.

The present invention provides a system including devices and methods that combine a means for occluding the aortic lumen to isolate the heart from the remainder of the arterial system with a means for introducing an endovascular device into the heart or the blood vessels of the heart. This combination provides a number of advantages not contemplated by the prior art. Namely, the invention allows the combination of diagnostic and therapeutic endovascular procedures with cardiopulmonary bypass and cardioplegic arrest in a manner that facilitates rather than inhibits the performance of both procedures. That is to say that the isolation of the heart and its blood vessels necessary for cardioplegia and cardiopulmonary support can be accomplished entirely through endovascular means without the necessity of a gross thoracotomy, and that, simultaneously, a path is created for introduction for one or more devices for performing a diagnostic or therapeutic endovascular procedure.

Endovascular procedures which lend themselves to this approach include diagnostic procedures, such as visualization of internal cardiac or vascular structures by optical or ultrasonic means or electrophysiological mapping of the heart, and therapeutic procedures, such as valvuloplasty, angioplasty, atherectomy, thrombectomy, stent placement, laser angioplasty, transmyocardial revascularization, or ablation of electrophysiological structures within the heart.

SUMMARY OF THE INVENTION

In keeping with the foregoing discussion, the present invention takes the form of a system that includes an endoaortic catheter for inducing cardioplegic arrest in the heart of a patient and at least one endovascular device which is slidably received within a lumen of the endoaortic catheter for performing an endovascular procedure on the patient's heart or blood vessels. A cardiopulmonary bypass (CPB) system, such as a femoral-femoral CPB system, may be used in conjunction with the endoaortic catheter for supporting the systemic circulation of the patient while the heart is stopped. The endovascular procedure can be performed as the sole procedure on the patient or it can be performed in conjunction with another cardiac surgical procedure, such as a port-access CABG procedure or heart valve replacement procedure, as described in the parent applications. The endovascular procedure can be carried out on the patient's heart while it is stopped or it can be performed on the beating heart in order to reduce the time that the heart is stopped (often referred to as the crossclamp time.)

The endoaortic partitioning catheter which is the foundation of the system for performing endovascular procedures is introduced percutaneously or by direct cut-down through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon may be of a cylindrical, spherical, football-shaped or other appropriate shape to fully and evenly accommodate the lumen of the ascending aorta. This maximizes the surface area contact with the aorta, and allows for even distribution of occlusive pressure.

The balloon of the catheter is in fluid communication with an inflation lumen that extends the length of the catheter. The balloon is preferably inflated with a saline solution to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg, for example, has been proven effective. The endoaortic partitioning catheter is preferably introduced under fluoroscopic guidance over a suitable guidewire. Transoesophageal echocardiography can alternatively be used for positioning the aortic catheter. The catheter may serve a number of separate functions and the number of lumina in the catheter will depend upon how many of those functions the catheter is to serve. The catheter can be used to introduce the cardioplegic agent, normally in solution, into the aortic root via a perfusion lumen. The luminal diameter will preferably be such that a flow of the order of 250–500 ml/min of cardioplegic solution can be introduced into the aortic root under positive pressure to perfuse adequately the heart by way of the coronary arteries. The same lumen can, by applying negative pressure to the lumen from an outside source, effectively vent the left heart of blood or other solutions.

In addition, the endoaortic partitioning catheter is adapted for introduction of one or more endovascular devices through an internal lumen of the catheter. This may be a separate lumen from the inflation lumen and the perfusion lumen discussed above or, for simplicity of construction and to maximize the potential lumen diameter, the perfusion lumen may be combined with the lumen for introduction of endovascular devices. It is preferable that the diameter and cross-sectional design of the internal lumina are such that the external diameter of the catheter in its entirety is small enough to allow its introduction into the adult femoral artery by either percutaneous puncture or direct cut-down.

In a first aspect of the invention, the system for performing endovascular procedures combines the endoaortic partitioning catheter with a fiberoptic angioscope for observation of structures within the heart and its blood vessels. In a second aspect, the endoaortic partitioning catheter is combined with a valvuloplasty system for correction of valvular stenosis in the aortic or mitral valve of the heart. In a third aspect, the endoaortic partitioning catheter is combined with an angioplasty system for therapeutic dilatation of coronary artery stenoses. In a fourth aspect, the endoaortic partitioning catheter is combined with a stent delivery catheter system for dilatation and stenting of coronary artery stenoses. In a fifth aspect, the endoaortic partitioning catheter is combined with an atherectomy system for removal of atheromatous material from within coronary artery stenoses. In a sixth aspect, the endoaortic partitioning catheter is combined with an intravascular ultrasonic imaging system for observation of structures and diagnosis of disease conditions within the heart and its associated blood vessels. In a seventh aspect, the endoaortic partitioning catheter is combined with a fiberoptic laser angioplasty system for removal of atheromatous material from within coronary artery stenoses. In an eighth aspect, the endoaortic partitioning catheter is combined with a side-firing fiberoptic laser catheter for performing transmyocardial revascularization from within the chambers of the heart. In a ninth aspect, the endoaortic partitioning catheter is combined with an electrophysiology mapping and ablation catheter for diagnosing and treating electrophysiological conditions of the heart.

A number of important advantages accrue from the combination of the endoaortic partitioning catheter with these endovascular diagnostic and therapeutic devices. Introducing endovascular devices through a lumen of the endoaortic partitioning catheter allows the patient's heart to be stopped and the circulatory system supported on cardiopulmonary bypass while performing the endovascular procedure. This may allow the application of various endovascular procedures to patients whose cardiac function is highly compromised and therefore might not otherwise be good candidates for the procedure. It also allows the endovascular procedures to be performed as an adjunct to other cardiac surgical procedures. With the devices of the prior art, it would be difficult to perform many of these endovascular procedures as an adjunct to cardiac surgery because the standard aortic crossclamps used entirely occlude the lumen of the aorta preventing the endovascular devices from being introduced through the normal transluminal route. Many of the diagnostic or therapeutic endovascular procedures will also benefit from performing the procedures while the heart is still and with no blood flow through the heart that would complicate the procedures. For instance ablation of anomalous structures such as calcification or scarring of the heart valves or laser ablation of abnormal electrophysiological foci can be more precisely and accurately controlled.

In an alternate mode of operation the endoaortic partitioning catheter can be used as a guiding catheter for introducing an endovascular device and for performing an endovascular procedure while the patient is on partial cardiopulmonary support without inflating the occlusion balloon or inducing cardiac arrest. If and when it is desired, the endoaortic partitioning catheter can be activated to occlude the aorta and induce cardioplegia, thereby converting the patient from partial cardiopulmonary support to full cardiopulmonary bypass. This mode of operation would be advantageous when it was desired to follow the endovascular procedure with another surgical procedure on the heart using either a thoracoscopic or standard open chest approach. It would also be advantageous when performing a high risk interventional procedure so that, in the event of complications, the patient can be immediately placed on full cardiopulmonary bypass and prepared for emergency surgery without delay. These and other advantages of the present invention will become apparent from reading and understand the following detailed description along with the accompanying drawings.

BRIEF DESCRIPTION OF THE DRAWINGS

FIG. 2A is a side elevation view of a first embodiment of an endoaortic partitioning device for partitioning the ascending aorta between the coronary ostia and brachiocephalic artery constructed in accordance with the principles of the present invention. FIG. 2B is an end view of a distal portion of the device of FIG. 2A illustrating the skew of the shaped distal portion. FIG. 2C is a transverse cross section taken along the line 2C—2C in FIG. 2A. FIG. 2D illustrates the deflated and inflated profile of one preferred embodiment of the elastomeric balloon of the endoaortic partitioning device. FIG. 2E illustrates another preferred embodiment of the elastomeric balloon of the endoaortic partitioning catheter.

FIG. 3A is a side elevation view of a second embodiment of an endoaortic partitioning device constructed in accordance with the principles of the present invention. FIG. 3B is a transverse cross section of the partitioning device of FIG. 3A taken along the line 3B—3B.

FIGS. 5A–5E shows a fourth embodiment of the endoaortic partitioning device which is coupled to an arterial bypass cannula so as to allow both the partitioning device and the cannula to be introduced through a single arterial puncture.

DETAILED DESCRIPTION OF THE INVENTION

The invention provides a system for performing endovascular procedures including an endoaortic device for partitioning the ascending aorta in combination with an endovascular device for performing a diagnostic or therapeutic endovascular procedure within the heart or blood vessels of a patient. The system may also include a means for selectively arresting the heart, such as a means for retrograde or antegrade infusion of cardioplegic fluid for inducing cardioplegic arrest. The invention is especially useful in conjunction with minimally-invasive cardiac procedures, in that it allows the heart to be arrested and the patient to be placed on cardiopulmonary bypass using only endovascular devices, obviating the need for a thoracotomy or other large incision. The procedures with which the invention will find use include diagnostic procedures, such as visualization of internal cardiac or vascular structures by optical or ultrasonic means or electrophysiological mapping of the heart, and therapeutic procedures, such as valvuloplasty, angioplasty, atherectomy, thrombectomy, stent placement, laser angioplasty, transmyocardial revascularization, or ablation of electrophysiological structures within the heart. The endovascular procedure which is performed using the systems and methods of the invention may be the primary procedure performed on the patient, or, alternatively, the endovascular procedure may be performed as an adjunct to another endovascular, thoracoscopic or open heart procedure.

Figure 1:
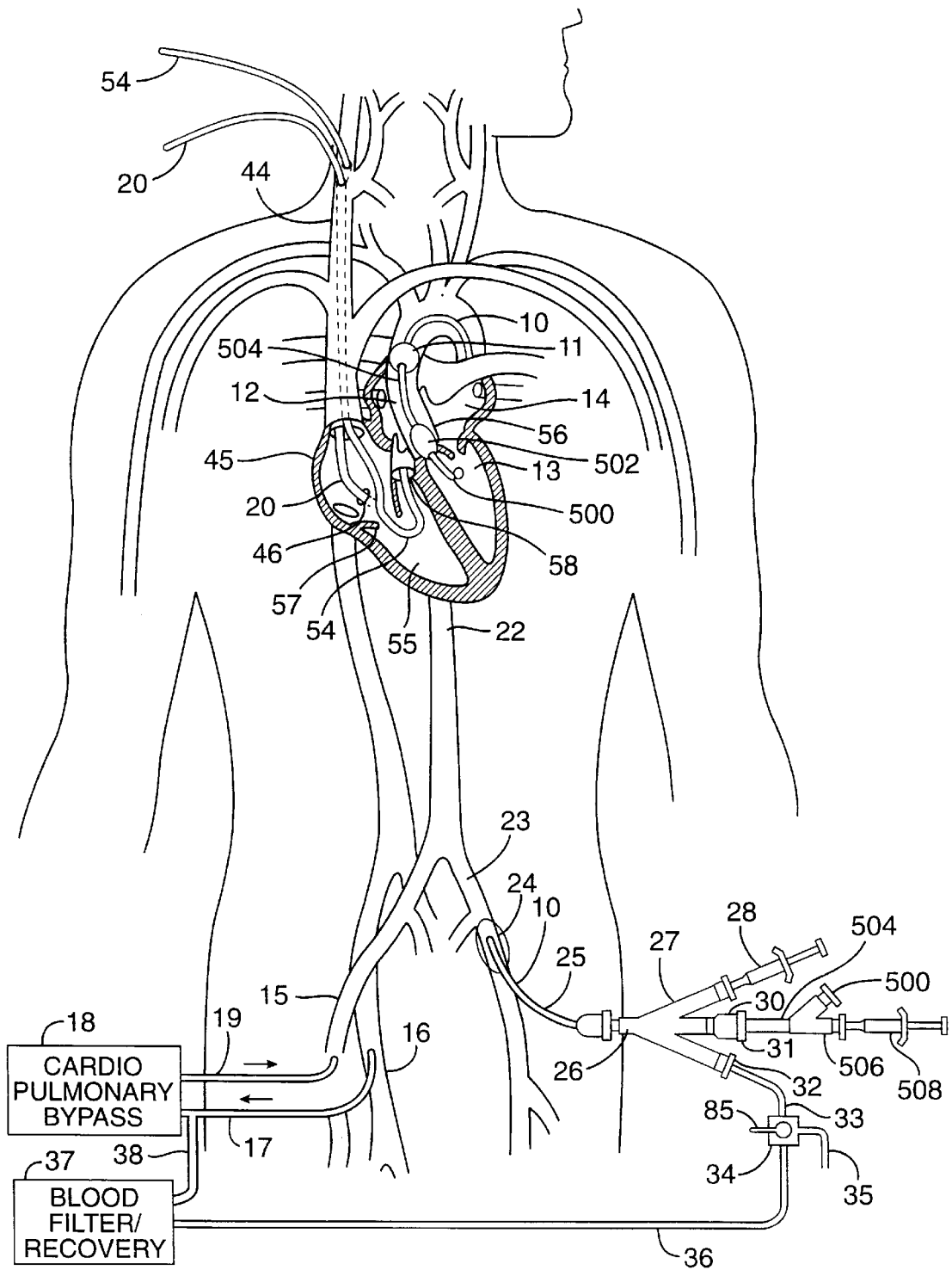
FIG. 1 schematically illustrates a system for performing endovascular procedures embodying features of the invention.

Reference is made to FIG. 1 which schematically illustrates the overall system for performing endovascular procedures of the invention and the individual components thereof. The endovascular procedure system includes an elongated aortic occlusion or delivery catheter 10 which has an expandable member 11 on a distal portion of the catheter which, when inflated as shown, occludes the ascending aorta 12 to separate the left ventricle 13 and upstream portion of the ascending aorta from the rest of the patient's arterial system and securely positions the distal end of the catheter within the ascending aorta. An endovascular device for performing a diagnostic or therapeutic procedure, represented here by a valvuloplasty catheter 500, is slidably received within an internal lumen of the aortic occlusion catheter 10. A cardiopulmonary bypass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. A fluid containing cardioplegic agents can be delivered through an internal lumen of the endoaortic occluding catheter in an antegrade manner into the aortic root and into the coronary arteries to paralyze the myocardium. Alternatively, a retrograde cardioplegia balloon catheter 20 may be placed within the patient's venous system with the distal end of the catheter extending into the coronary sinus 21 to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with a main access port having a hemostasis valve 31 through which the endovascular device 500 is inserted into internal lumen of the aortic occlusion catheter 10. The function of the hemostasis valve 31 may also be provided by a separate adapter which connects to second arm 30 of the multi-arm adapter 26. A third arm 32 connected to bypass line 33 is provided to direct blood, irrigation fluid, and the like to or from the system. A suitable valve 34 is provided to open and close the bypass line 33 and direct the fluid passing through the bypass line to a discharge line 35 or a line 36 to a blood filter and recovery unit 37. A return line 38 may be provided to return any filtered blood, which will be described hereinafter, to the cardiopulmonary bypass system 18 or other blood conservation system.

Figure 7:
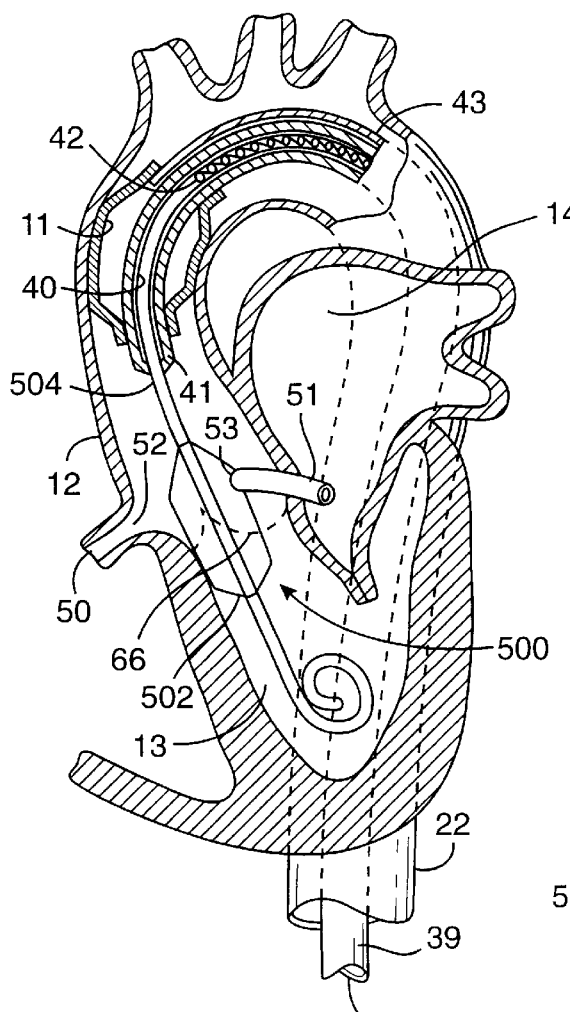
FIG. 7 is a view of a patient's heart with the endoaortic partitioning device placed in the ascending aorta and with a valvuloplasty balloon catheter inflated within the aortic valve.

The details of the aortic occlusion catheter 10 and the disposition of the distal extremity thereof within the aorta are best illustrated in FIG. 7. As indicated, the catheter 10 includes an elongated catheter shaft 39 which has a first inner lumen 40 in fluid communication with the main access port 31 in the second arm of the adapter 26 and is adapted to facilitate the passage of an endovascular device, again represented by a valvuloplasty catheter 500, out the distal port 41 in the distal end thereof. A supporting coil 42 may be provided in the distal portion of the first inner lumen 40 to prevent the catheter shaft 39 from kinking and to enhance radial rigidity and to maintain the transverse dimensions of first inner lumen 40 as the catheter 10 is advanced through the aortic arch. It is particularly important to maintain the roundness of first inner lumen 40 where an endovascular device is to be introduced through the first inner lumen. If the shaft is made of sufficient diameter to accommodate such tools through lumen 40, the shaft may tend to flatten or kink when advanced into the curved region of the aortic arch. The use of wire braid or coil 42 to maintain lumen roundness allows the endovascular device profile to be maximized and allows endovascular devices to be advanced through the lumen with minimum interference. Wire braid or coil 42 may be formed of stainless steel or other biocompatible material such as a cobalt alloy, nickel titanium alloy, aramid fibers such as Kevlar™ (DuPont), or nylon. The shaft 39 is also provided with a second inner lumen 43 which is in fluid communication with the interior of the occluding balloon 11.

Turning now to FIGS. 2–4, several additional exemplary embodiments of an endovascular device for partitioning the ascending aorta according to the invention will be described. As illustrated in FIG. 2A, partitioning device 320 includes a shaft 322 having a distal end 324 and a proximal end 326. An expandable means 328 for occluding the ascending aorta is mounted to shaft 322 near distal end 324. In a preferred embodiment, occluding means 328 comprises a polymeric balloon 330 (shown inflated) of a material, geometry, and dimensions suitable for completely occluding the ascending aorta to block systolic and diastolic blood flow, as described more fully below.

Shaft 322 has a diameter suitable for introduction through a femoral or iliac artery, usually less than about 9 mm. The length of shaft 322 is preferably greater than about 80 cm, usually about 90–100 cm, so as to position balloon 330 in the ascending aorta between the coronary ostia and the brachiocephalic artery with proximal end 326 disposed outside of the body, preferably from the femoral or iliac artery in the groin area. Alternatively, the shaft may be configured for introduction through the carotid artery, through the brachial artery, or through a penetration in the aorta itself, wherein the shaft may have a length in the range of 20 to 60 cm.

Partitioning device 320 further includes a first inner lumen 329, extending between proximal end 326 and distal end 324 with an opening 331 at distal end 324. Additional openings in communication with inner lumen 329 may be provided on a lateral side of shaft 322 near distal end 324.

Shaft 322 has a shaped distal portion 332 configured to conform generally to the curvature of the aortic arch such that opening 331 at distal end 324 is spaced apart from the interior wall of the aorta and is axially aligned with the center of the aortic valve. Usually, shaped distal portion 332 will be generally U-shaped, such that a distal segment 334 is disposed at an angle between 135° and 225°, and preferably at approximately 180° relative to an axial direction defined by the generally straight proximal segment 336 of shaft 322. Shaped distal portion 332 will usually have a radius of curvature in the range of 20–80 mm (measured at the radial center of shaft 322), depending upon the size of the aorta in which the device is used. The configuration of shaped distal portion 332 allows distal segment 334 to be positioned centrally within the lumen of the ascending aorta and distal end 324 to be axially aligned with the center of the aortic valve, thereby facilitating infusion or aspiration of fluids as well as introduction of surgical tools through opening 331 without interference with the wall of the aorta, as described more fully below.

In an exemplary embodiment, shaped distal portion 332 is preshaped so as to maintain a permanent, generally U-shaped configuration in an unstressed condition. Such a preshaped configuration may be formed by positioning a mandrel having the desired shape in first inner lumen 329, then baking or otherwise heating shaft 322 and the mandrel for a sufficient time and sufficient temperature to create a permanent set therein, e.g., 1–3 hours at a temperature in a range of 120° C. to 180° C., depending upon the material used for shaft 322.

In alternative embodiments, the U-shaped distal portion 332, rather than having a continuous, constant curvature, may be preshaped in a more angular fashion, with bends of relatively small curvature separating segments which are either straight or of larger curvature. The bends and/or segments may further be configured to engage the inner wall of the aortic arch to deflect distal end 324 into a desired position in the ascending aorta. Alternatively, shaped distal portion 332 may be configured in a general "S" shape for introduction into the ascending aorta from a location superior to the aortic arch. In this way, distal segment 334 may be positioned within the ascending aorta, with proximal segment 336 extending from the aortic arch through the brachiocephalic artery to the carotid or brachial artery, or through a penetration in the aorta itself, to a point outside of the thoracic cavity.

As shown in FIG. 2B, distal segment 334 may be skewed (non-coplanar) relative to a central longitudinal axis of proximal segment 336, in order to further conform to the shape of the patient's aortic arch and align with the center of the aortic valve. In an exemplary embodiment, distal segment 334 is disposed at an angle a relative to a plane containing the central axis of proximal portion 336, wherein a is between 2° and 30°, usually between 10° and 20°, and preferably about 15°. The shape and dimensions of shaped distal portion 332 and angle a of distal segment 334 may vary, however, according to the configuration of the aortic arch in any individual patient.

In a preferred embodiment, the device will include a soft tip 338 attached to distal end 324 to reduce the risk of damaging cardiac tissue, particularly the leaflets of the aortic valve, in the event the device contacts such tissue. Soft tip 338 may be straight or tapered in the distal direction, with an axial passage aligned with opening 331 at the distal end of shaft 322. Preferably, soft tip 338 will be a low durometer polymer such as polyurethane or Pebax, with a durometer in the range of 65 Shore A to 35 Shore D.

At least one radiopaque stripe or marker 339 is preferably provided on shaft 322 near distal end 324 to facilitate fluoroscopic visualization for positioning balloon 330 in the ascending aorta. Radiopaque marker 339 may comprise a band of platinum or other radiopaque material. Alternatively, a filler of barium or bismuth salt may be added to the polymer used for shaft 322 or soft tip 338 to provide radiopacity.

As illustrated in FIG. 2A, a straightening element 340 is disposed in first inner lumen 329 of shaft 322 so as to slide longitudinally relative to the shaft. Straightening element 340 may comprise a tubular stylet with a longitudinal passage 344 for receiving a guidewire 342, as described below. Alternatively, element 340 may comprise a relatively stiff portion of the guidewire itself. Straightening element 340 may be a polymeric material or a biocompatible metal such as stainless steel or nickel titanium alloy with a bending stiffness greater than that of shaft 322. In this way, straightening element 340 may be advanced distally into preshaped distal portion 332 so as to straighten shaft 322, facilitating subcutaneous introduction of partitioning device 320 into an artery and advancement to the aortic arch. Straightening element 340 may then be retracted proximally relative to the shaft so that distal end 324 can be positioned in the ascending aorta with preshaped distal portion 332 conforming to the shape of the aortic arch.

A movable guidewire 342 is slidably disposed through first inner lumen 329, either through longitudinal passage 344 in straightening element 340, external and parallel to straightening element 340, or through a separate lumen in shaft 322. Guidewire 342 extends through opening 331 in distal end 324 of shaft 322 and may be advanced into an artery distal to shaft 322, facilitating advancement of shaft 322 through the artery to the ascending aorta by sliding the shaft over the guidewire. In an exemplary embodiment, guidewire 342 is relatively stiff so as to at least partially straighten shaft 322, so that straightening element 340 is unnecessary for introduction of shaft 322. In this embodiment, guidewire 342 may be, for example, stainless steel or a nickel titanium alloy with a diameter of about 1.0 mm to 1.6 mm.

Shaft 322 may have any of a variety of configurations depending upon the particular procedure to be performed. In one embodiment, shaft 322 has a multi-lumen configuration with three non-coaxial parallel lumens in a single extrusion, as illustrated in FIG. 2C. The three lumens include first inner lumen 329, which receives straightening element 340 and guidewire 342 and includes opening 331 at its distal end, an inflation lumen 346 which opens at an inflation orifice 347 near the distal end of shaft 322 in communication with the interior of balloon 330, and a third lumen 348 which has an opening (not shown) at distal end 324 of the shaft to sense pressure in the ascending aorta upstream of balloon 330. In this embodiment, the largest transverse dimension of first inner lumen 329 is preferably about 1 mm–4 mm. Advantageously, the distal opening in third lumen 348 is radially offset from opening 331 in first inner lumen 329, so that infusion or aspiration of fluid through first inner lumen 329 will not affect pressure measurements taken through third lumen 348.

It should be noted that where partitioning device 320 is to be utilized for antegrade delivery of cardioplegic fluid through first inner lumen 329, it will be configured to provide a sufficient flowrate of such fluid to maintain paralysis of the heart, while avoiding undue hemolysis in the blood component (if any) of the fluid. In a presently preferred embodiment, cold blood cardioplegia is the preferred technique for arresting the heart, wherein a cooled mixture of blood and a crystalloid KCl/saline solution is introduced into the coronary arteries to perfuse and paralyze the myocardium. The cardioplegic fluid mixture is preferably run through tubing immersed in an ice bath so as to cool the fluid to a temperature of about 3° C.–10° C. prior to delivery through inner lumen 329. The cardioplegic fluid is delivered through inner lumen 329 at a sufficient flowrate and pressure to maintain a pressure in the aortic root (as measured through third lumen 348) high enough to induce flow through the coronary arteries to perfuse the myocardium. Usually, a pressure of about 50–100 mmHg, preferably 60–70 mmHg, is maintained in the aortic root during infusion of cardioplegic fluid, although this may vary somewhat depending on patient anatomy, physiological changes such as coronary dilation, and other factors. At the same time, in pumping the cardioplegic fluid through inner lumen 329, it should not be subject to pump pressures greater than about 300 mmHg, so as to avoid hemolysis in the blood component of the fluid mixture. In an exemplary embodiment, first inner lumen 329 is configured to facilitate delivery of the cardioplegic fluid at a rate of about 250–350 ml/min. preferably about 300 ml/min., under a pressure of no more than about 300 ml/min, enabling the delivery of about 500–1000 ml of fluid in 1–3 minutes. To provide the desired flowrate at this pressure, inner lumen 329 usually has a cross-sectional area of at least about 4.5 mm$^2$, and preferably about 5.6–5.9 mm$^2$. In an exemplary embodiment, D-shaped lumen 329 in FIG. 2C has a straight wall about 3.3 mm in width, and a round wall with a radius of about 1.65 mm. A completely circular lumen 329 (not pictured), could have an inner diameter of about 2.7 mm. Inner lumen 329 could be significantly smaller, however, if the cardioplegic fluid did not have a blood component so that it could be delivered under higher pressures without risk of hemolysis. Because of its myocardial protective aspects, however, the aforementioned blood/KCl mixture is presently preferred, requiring a somewhat larger lumen size than would be required for a crystalloid KCl cardioplegic fluid without blood.

Shaft 322 may be constructed of any of a variety of materials, including biocompatible polymers such as polyurethane, polyvinyl chloride, polyether block amide, or polyethylene. In a preferred embodiment of the device shown in FIG. 2A, shaft 322 is urethane with a shore durometer in the range of 50 D–100 D. Shaft 322 may have a bending modulus in the range of 70 to 100 kpsi, preferably about 80–90 kpsi. A bending modulus in this range provides sufficient stiffness to optimize pushability from a femoral or iliac artery to the ascending aorta, while providing sufficient flexibility to navigate the tortuous iliac artery and the aortic arch. Once partitioning device 320 has been positioned with distal end 324 in the ascending aorta, this bending modulus also facilitates exertion of a distally-directed force on shaft 322 from proximal end 326 to maintain the position of balloon 330 against the outflow of blood from the left ventricle as the balloon is inflated. In other embodiments, the dimensions, geometry and/or materials of shaft 322, as well as coil 360, may be varied over the length of the shaft so that the shaft exhibits variable bending stiffness in various regions. For example, preshaped distal portion 332 may be more flexible for tracking through the aortic arch, whereas proximal portion 336 may be stiffer for pushability and resistance to displacement. Balloon 330 may be constructed of various materials and in various geometries. In a preferred embodiment, balloon 330 has a collapsed profile small enough for introduction into the femoral or iliac artery, e.g. 4–9 mm outside diameter, and an expanded (inflated) profile large enough to completely occlude the ascending aorta, e.g. 20–40 mm outside diameter. The ratio of expanded profile diameter to collapsed profile diameter will thus be between 2 and 10, and preferably between 5 and 10. The balloon is further configured to maximize contact of the working surface of the balloon with the aortic wall to resist displacement and to minimize leakage around the balloon, preferably having a working surface with an axial length in the range of about 3 cm to about 7 cm when the balloon is expanded. Textural features such as ribs, ridges or bumps may also be provided on the balloon working surface for increased frictional effects to further resist displacement.

Balloon 330 preferably has some degree of radial expansion or elongation so that a single balloon size may be used for aortas of various diameters. Materials which may be used for balloon 330 include polyurethanes, polyethylene terephthalate (PET), polyvinyl chloride (PVC), polyolefin, latex, ethylene vinyl acetate (EVA) and the like. However, balloon 330 must have sufficient structural integrity when inflated to maintain its general shape and position relative to shaft 322 under the systolic pressure of blood flow through the ascending aorta. In an exemplary embodiment, balloon 330 is constructed of polyurethane or a blend of polyurethane and polyvinyl such as PVC. It has been found that such materials have sufficient elastic elongation to accommodate a range of vessel diameters, while having sufficient structural integrity to maintain their shape and position in the ascending aorta when subject to outflow of blood from the left ventricle. In other preferred embodiments, balloon may be further provided with a plurality of folds or pleats which allow the balloon to be collapsed by evacuation to a small collapsed profile for introduction into a femoral or iliac artery.

FIG. 2D illustrates the deflated and inflated profile of one preferred embodiment of the elastomeric balloon 330 of the endoaortic partitioning catheter 320. The deflated profile 330' has an oblong or football shape which is imparted by the balloon molding process. The wall thickness of the molded balloon 330' in its deflated state is typically about 0.090–0.130 mm. The deflated balloon 330' has a diameter of approximately 12 mm. The inflated balloon 330 assumes a roughly spherical shape with a maximum diameter of approximately 40 mm when inflated. The football shape of the molded balloon has been shown to be advantageous in that the deflated balloon 330' has a deflated profile which is less bulky and smoother than for other balloon geometries tested. This allows the deflated balloon 330' to be folded and more easily inserted through a percutaneous puncture into the femoral artery or through an introducer sheath or a dual arterial cannula/introducer sheath. Other acceptable geometries for the molded elastomeric balloon 330 include a simple cylinder, an enlarged cylinder with tapered ends or a spherical shape.

FIG. 2E illustrates another preferred embodiment of the elastomeric balloon 330 of the endoaortic partitioning catheter 320. After molding, the distal end 200 of the deflated balloon 300' is inverted and adhesively attached to the distal end 202 of the catheter shaft 322. When the balloon is inflated to its inflated profile 330, the distal end 202 of the catheter shaft 322 is protected by the inflated balloon 330 and prevented from touching the aortic valve or the aortic walls, obviating the need for the soft tip 338 of the embodiment of FIGS. 2A, 2B and 2D.

Referring again to FIG. 2A, a triple-arm adapter 364 is attached to the proximal end 326 of shaft 322. Triple-arm adapter 364 includes a working port 366 in communication with first inner lumen 329 through which straightening element 340 and guidewire 342, may be introduced, to straighten the shaft 322 to facilitate introduction of the catheter 320 into the femoral artery. Once the catheter is positioned within the ascending aorta of the patient, the straightening element 340 and guidewire 342 may be withdrawn to allow introduction of an endovascular device through the working port 366 into the first inner lumen 329 of the catheter. Working port 366 may also be adapted for infusion of fluid such as cardioplegic fluid, saline or contrast solution, as well as for aspiration of blood, fluids and debris through first inner lumen 329. Triple-arm adapter 364 further includes an inflation port 368 in communication with the inflation lumen and configured for connection to an inflation fluid delivery device such as a syringe 370 or other commercially available balloon-inflation device such as the Indeflator™ available from Advanced Cardiovascular Systems, Inc. of Santa Clara, Calif. A pressure measurement port 372 is in communication with the third lumen (348 or 354) and is adapted for connection to a pressure measurement device. Alternatively, where shaft 322 includes only first inner lumen 329 and inflation lumen 358 as in FIGS. 26B, 28 and 30, port 372 may be in communication with first inner lumen 329 and configured for pressure measurement, fluid infusion or aspiration.

A second alternative embodiment of partitioning device 320 is illustrated in FIGS. 3A–3B. In this embodiment, shaft 322 is positionable in an interior lumen 420 of a guiding catheter 422. Device 320 may be configured as described above in reference to FIG. 2A, including balloon 330 near distal end 324, inner lumen 329, inflation lumen 346, pressure lumen 348, soft tip 338 attached to distal end 324, and triple-arm adapter 364 attached to proximal end 326. Guiding catheter 422 has a proximal end 424 and a distal end 426, with axial lumen 420 extending therebetween. A soft tip (not shown) may be attached to distal end 426 to minimize injury to the aorta or aortic valve in the event of contact therewith. A proximal adapter 428 is attached to proximal end 424, and has a first port 430 in communication with lumen 420 through which shaft 322 may be introduced, and a second port 432 in communication with lumen 420 for infusing or aspirating fluid. Port 430 may further include a hemostasis valve. Guiding catheter 422 also has a distal portion 434 which is either preshaped or deflectable into a shape generally conforming to the shape of the aortic arch. Techniques suitable for preshaping or deflecting distal portion 434 of guiding catheter 422 are described above in connection with FIGS. 2A and 2B. In an exemplary embodiment, guiding catheter 422 is preshaped in a generally U-shaped configuration, with a radius of curvature in the range of 20–80 mm. In this embodiment, a stylet (not shown) like that described above in connection with FIGS. 25–30 is provided for straightening distal portion 434 for purposes of percutaneously introducing guiding catheter 422 into an artery.

In use, guiding catheter 422 is introduced into an artery, e.g. a femoral or iliac artery, and advanced toward the heart until distal end 426 is in the ascending aorta. A guidewire (not shown) may be used to enhance tracking. Where a stylet is used to straighten a preshaped guiding catheter for subcutaneous introduction, the stylet is withdrawn as preshaped distal portion 434 is advanced through the aortic arch. Once guiding catheter 422 is in position, shaft 322 may be introduced through port 430 and lumen 420 and advanced toward the heart until balloon 330 is disposed between the coronary ostia and the brachiocephalic artery, distal to the distal end 426 of guiding catheter 422. The distal portion 332 of shaft 322 is shaped to conform to the aortic arch by preshaped portion 434 of guiding catheter 422. Balloon 330 is then inflated to fully occlude the ascending aorta and block blood flow therethrough.

Figure 4A:
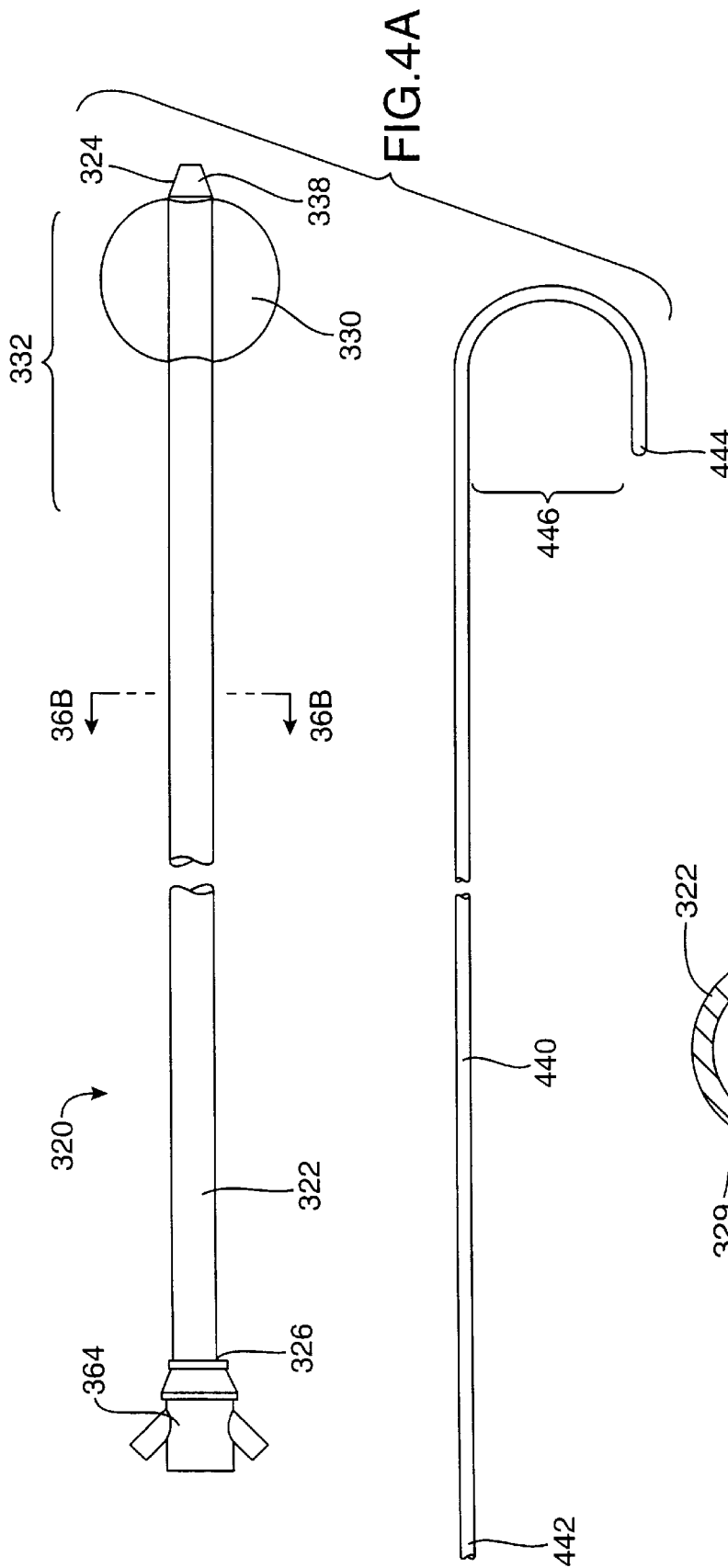
FIG. 4A is a side elevation view of a third embodiment of an endoaortic partitioning device constructed in accordance with the principles of the invention.
Figure 4B:
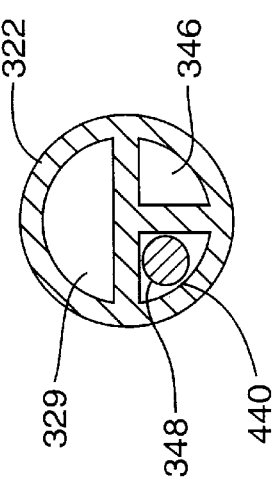
FIG. 4B is a transverse cross section taken along the line 4B—4B in FIG. 4A, showing a shaping element positioned in an inner lumen in the shaft.

In a third embodiment, shown in FIGS. 4A–4B, partitioning device 320 includes a shaping element 440 positionable in a lumen in shaft 322, such as third inner lumen 348. Shaping element 440 has a proximal end 442, a distal end 444 and a preshaped distal portion 446. Preshaped distal portion 446 may be generally U-shaped as illustrated, or may have an angular, "S"-shaped or other configuration in an unstressed condition, which will shape distal portion 332 to generally conform to at least a portion of the patient's aortic arch. Shaping element 440 is preferably stainless steel, nickel titanium alloy, or other biocompatible material with a bending stiffness greater than that of shaft 322 so as to deflect distal portion 332 into the desired shape. Shaping element 440 may be a guidewire over which shaft 322 is advanced to the ascending aorta, or a stylet which is inserted into third inner lumen 348 after shaft 322 is positioned with balloon 330 in the ascending aorta. In a preferred embodiment, shaping element 440 is configured to position distal end 324 of shaft 322 in a radial position within the ascending aorta to be spaced apart from the interior wall thereof, and in particular, axially aligned with the center of the aortic valve.

In a further aspect of the invention, illustrated in FIGS. 5A–5E, partitioning device 320 is coupled to an arterial bypass cannula 450 so as to allow both device 320 and cannula 450 to be introduced through the same arterial puncture. Arterial bypass cannula 450 is configured for connection to a cardiopulmonary bypass system for delivering oxygenated blood to the patient's arterial system. Arterial bypass cannula 450 has a distal end 452, a proximal end 454, a blood flow lumen 456 extending between proximal end 454 and distal end 452, and an outflow port 458 at distal end 452. A plurality of additional outflow ports 460 may be provided along the length of arterial bypass cannula 450, particularly near distal end 452. In a preferred embodiment, arterial bypass cannula 450 has a length between about 10 cm and 60 cm, and preferably between about 15 cm and 30 cm.

An adaptor 462 is connected to proximal end 454 of bypass cannula 450, and includes a first access port 464 and a second access port 466, both in fluid communication with blood flow lumen 456. Access port 466 is configured for fluid connection to tubing from a cardiopulmonary bypass system, and preferably has a barbed fitting 468. Access port 464 is configured to receive partitioning device 320 therethrough. Preferably, a hemostasis valve 470, shown in FIG. 5C, is mounted in access port 464 to prevent leakage of blood and other fluids through access port 464 whether or not shaft 322 of partitioning device 320 is positioned therein. Hemostasis valve 470 may have any number of well-known constructions, including, for example, an elastomeric disk 469 having one or more slits 472 through which shaft 422 may be positioned, and a diaphragm 471 adjacent to the disk with a central hole 474 for sealing around the periphery of shaft 322. A hemostasis valve of this type is described in U.S. Pat. No. 4,000,739, which is incorporated herein by reference. Other types of hemostasis valves may also be used, such as duck-bill valves, O-ring seals, and rotational or sliding mechanical valves. In addition, a Touhy-Borst valve 473 including a threaded, rotatable cap 475 may be provided on the proximal end of access port 464 to facilitate clamping and sealing around shaft 322 by tightening cap 475, which compresses O-rings 477 about shaft 322.

Shaft 322 of partitioning device 320 and blood flow lumen 456 of bypass cannula 450 are configured and dimensioned to facilitate sufficient blood flow through blood flow lumen 456 to support full cardiopulmonary bypass with complete cessation of cardiac activity, without an undesirable level of hemolysis. In a preferred embodiment, arterial bypass cannula 450 has an outer diameter of 6 mm to 10 mm, and blood flow lumen 456 has an inner diameter of 5 mm to 9 mm. Shaft 322 of partitioning device 320 has an outer diameter in the range of 2 mm to 5 mm. In this way, blood flow lumen 456, with shaft 322 positioned therein, facilitates a blood flow rate of at least about 4 liters/minute at a pump pressure of less than about 250 mmHg.

Arterial bypass cannula 450 is preferably introduced into an artery, usually a femoral artery, with partitioning device 320 removed from blood flow lumen 456. An obturator 476, illustrated in FIG. 5D, may be positioned in blood flow lumen 456 such that the tapered distal end 478 of obturator 476 extends distally from the distal end 452 of arterial bypass cannula 450. The arterial bypass cannula 450 may be introduced into the artery by various techniques including percutaneous methods such as the Seldinger technique, but is usually of sufficient size to require a surgical cutdown. A guidewire 480 may be slidably positioned through a lumen 482 in obturator 476 to facilitate introduction of arterial bypass cannula 450. Guidewire 480 is advanced into the artery through an arteriotomy, and arterial bypass cannula 450 with obturator 476 positioned therein is advanced into the artery over guidewire 480. Obturator 476 may then be removed, allowing partitioning device 320 to be introduced into the artery through blood flow lumen 456, usually over guidewire 480. Guidewire 480 may be advanced toward the heart and into the ascending aorta to facilitate positioning the distal end 324 of partitioning device 320 therein.

In one particularly preferred embodiment, which is shown in cross section in FIG. 5B, the shaft 322 of partitioning device 320 has an outer diameter of approximately 3.45 mm or 10.5 French (Charriere scale). The three lumen shaft 320 is extruded from a thermoplastic elastomer with a Shore D durometer of approximately 72. The D-shaped infusion lumen 329 has a height from the interlumen wall 702 to the exterior wall 700 of approximately 2.08 mm which allows sufficient flow rate for delivery of cardioplegic fluid and provides sufficient diametrical clearance for passage of an endovascular device through the infusion lumen 329 for performing an endovascular procedure within the heart or blood vessels of the patient. The balloon inflation lumen 346 in this embodiment has a width of approximately 1.40 mm, and the pressure monitoring lumen 348 has a width of approximately 0.79 mm. The interlumen wall 702 between the three lumens and the exterior wall 700 of the shaft 322 have a wall thickness of approximately 0.20 mm. When the 10.5 French shaft 322 is introduced through the blood flow lumen 456 of a 21 French (7.00 mm outer diameter) arterial bypass cannula 450, the blood flow lumen 456 allows a blood flow rate of approximately 5 liters/minute at a pump pressure of about 350 mmHg. When the 10.5 French shaft 322 is introduced through the blood flow lumen 456 of a 23 French (7.67 mm outer diameter) arterial bypass cannula 450, the blood flow lumen 456 allows a blood flow rate of approximately 6 liters/minute at a pump pressure of about 350 mmHg. The choice of what size arterial bypass cannula 450 to use for a given patient will depend on the size of the patient's femoral arteries and overall body size which determines the flow rate required.

In an alternative embodiment, arterial bypass cannula 450 may be configured so that partitioning device 320 is not removable from blood flow lumen 456. In this embodiment, bypass cannula 450 is introduced into an artery with partitioning device 320 positioned in blood flow lumen 456. Partitioning device 320 may be slidable within a limited range of movement within blood flow lumen 456. Alternatively, partitioning device 320 may be fixed to arterial bypass cannula 450 to prevent relative movement between the two. For example, shaft 322 may be extruded from the same tubing which is used to form arterial bypass cannula 450. Or, shaft 322 may be attached within the interior of blood flow lumen 456 or at the distal end 452 of arterial bypass cannula 450. Additionally, distal end 452 of bypass cannula 450 may be tapered to seal around shaft 322 and may or may not be bonded to shaft 322. In this configuration, side ports 460 permit outflow of blood from blood flow lumen 456.

Figure 6:
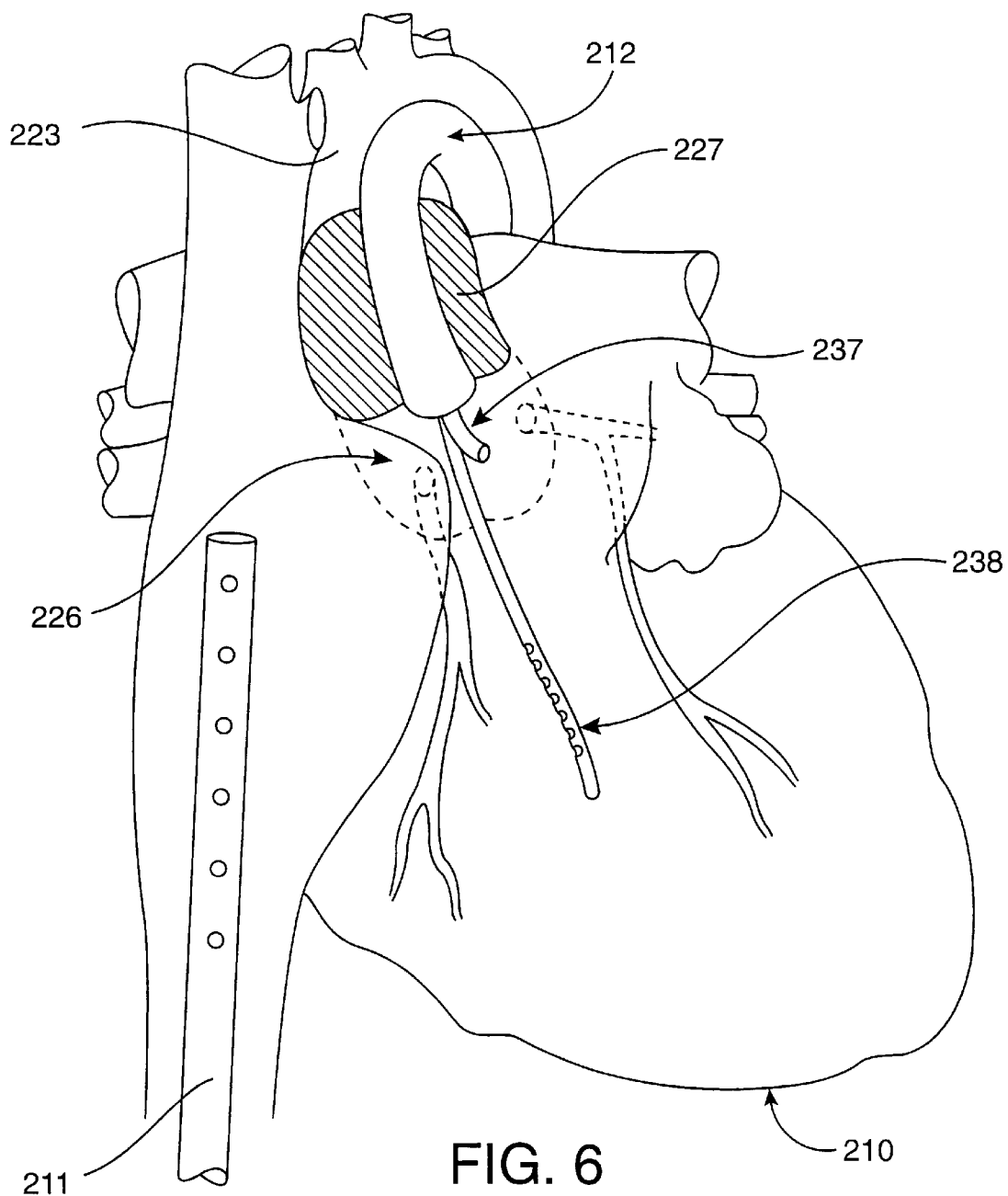
FIG. 6 is a schematic partly cut-away representation of a patient's heart with the endoaortic partitioning device percutaneously placed within the ascending aorta and with an angioscope and a left ventricular venting catheter introduced into the aortic root and left ventricle respectively, via separate lumina within the aortic partitioning device.

FIG. 6 shows a schematic representation of a patient's heart 210 partly cut-away to show some of the internal structures of the heart. The endoaortic partitioning device 212 has been percutaneously introduced into an artery, such as the femoral artery, by the Seldinger technique or an arterial cutdown and advanced into the ascending aorta 223. The occlusion balloon 227 is inflated within the ascending aorta 223 to occlude the aortic lumen and to separate the heart 210 and the aortic root 226 from the remainder of the circulatory system. Generally, the circulatory system is placed on cardiopulmonary bypass and the heart is stopped, as by infusion of a cardioplegic agent or by hypothermic arrest or other means, simultaneous with the inflation of the occlusion balloon 227. One or more endovascular devices are introduced through an internal lumen in the endoaortic partitioning device 212 to perform a diagnostic or therapeutic endovascular procedure within the heart or blood vessels of the patient.

In this illustrative example, a fiberoptic cardioscope or angioscope 237 has been introduced through the endoaortic partitioning device 212 into the aortic root 226 for visualizing the internal structures of the heart 210 and the blood vessels. The aortic root 226 and/or the chambers of the heart 210 and its blood vessels can be filled with a transparent liquid, for example saline solution or crystaloid cardioplegic solution, infused through a lumen in the endoaortic partitioning device 212 to displace the blood and provide a clear view of structures such as the aortic or mitral valve, the aortic root or the coronary arteries. The angioscope 237 can be used for diagnosis of insufficient, stenotic or calcified heart valves, atrial or ventricular septal defects, patent ductus arteriosus, coronary artery disease or other conditions. This endovascular prodedure may be performed in preparation for or for observation during a therapeutic procedure such as repair or replacement of a heart valve or as an adjunct to a concomitant procedure on the heart. In addition, FIG. 6 shows a left ventricular venting catheter 238 introduced into left ventricle of the heart 210 to vent blood and other fluids from the heart to relieve pressure that could cause distention of the heart while the patient is on cardiopulmonary bypass.

FIGS. 1 and 7 show another embodiment of the system for performing endovascular procedures of the present invention. The endoaortic partitioning device 10 has previously been introduced into the ascending aorta 12 and the occlusion balloon 11 inflated to occlude the aortic lumen, as described above. In this illustrative example, a valvuloplasty catheter 500 has been introduced through an internal lumen 40 of the endoaortic partitioning device 10, as shown in FIG. 1. The valvuloplasty catheter 500 has an expandable dilatation balloon 502 on the distal end of an elongated shaft 504. A fluid-filled syringe 508 or other inflation device is attached to a fitting 506 on the proximal end of the shaft 504. An inflation lumen within the shaft 504 connects the fitting 506 with the interior of the dilatation balloon 502. The dilatation balloon 502 is introduced through the lumen 40 of the endoaortic partitioning device 10 in a deflated condition until the dilatation balloon 502 emerges from the distal end 41 of the endoaortic partitioning device 10 into the aortic root. The dilatation balloon 502 is advanced across the patient's aortic valve 66 and the dilatation balloon 502 is expanded within the aortic valve 66, as shown in FIG. 7, to relieve a stenosis of the valve or to mobilize calcified valve leaflets. The dilatation balloon 502 is then deflated and the valvuloplasty catheter 500 is withdrawn from the patient.

Figure 8:
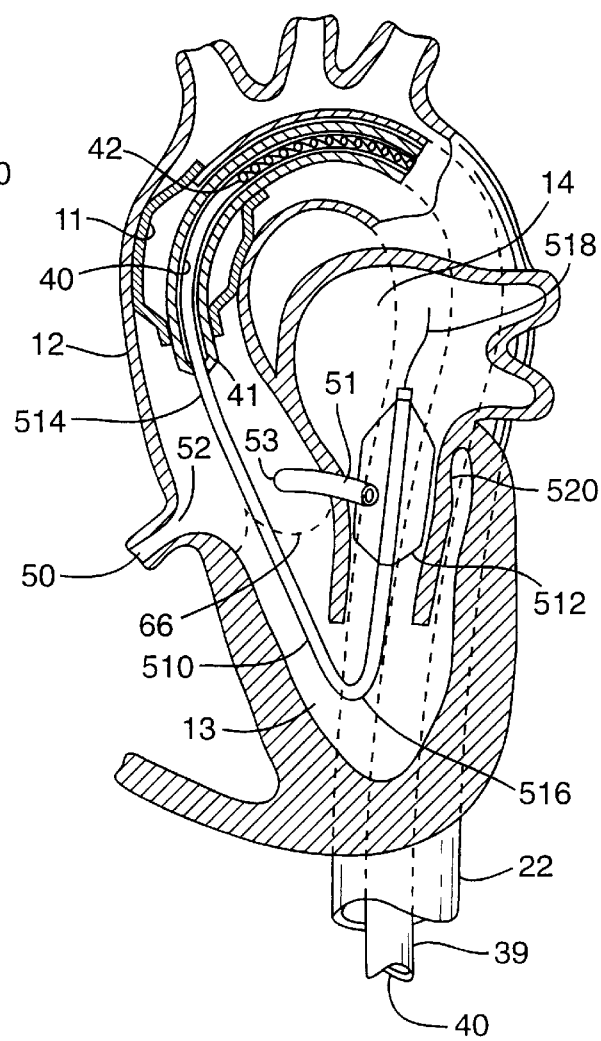
FIG. 8 is a view of a patient's heart with the endoaortic partitioning device placed in the ascending aorta and with a valvuloplasty balloon catheter inflated within the mitral valve.

FIG. 8 shows another embodiment of the system for performing endovascular procedures of the present invention. A mitral valvuloplasty catheter 510 has been introduced through the internal lumen 40 of the endoaortic partitioning device 10, past the aortic valve 66, into the left ventricle of the heart and across the mitral valve 520. The mitral valvuloplasty catheter 510 has an expandable dilatation balloon 512 on the distal end of an elongated shaft 514. A guidewire 518 which is slidably received within a lumen of the mitral valvuloplasty catheter 510 may be used to direct the catheter through the chambers of the heart into the mitral valve 520. In addition, the shaft 514 of the mitral valvuloplasty catheter 510 may be made with a preformed bend 516 that directs the distal end of the catheter through the mitral valve 520. The dilatation balloon 512 is expanded within the mitral valve 520, as shown in FIG. 8, to relieve a stenosis of the mitral valve. Then, the dilatation balloon 512 is then deflated and the valvuloplasty catheter 510 is withdrawn from the patient.

Performing a valvuloplasty procedure by introducing the balloon dilatation catheter through the endoaortic partitioning device allows the patient's heart to be stopped and the circulatory system supported on cardiopulmonary bypass during the valvuloplasty procedure. This may allow the application of valvuloplasty to patients whose cardiac function is highly compromised and therefore might not otherwise be good candidates for the procedure. It also allows valvuloplasty to be performed as an adjunct to other cardiac surgical procedures. For instance, aortic valve calcification is a condition which frequently accompanies coronary artery disease. However, it would be difficult to perform aortic valvuloplasty as an adjunct to a coronary artery bypass procedure using a standard aortic crossclamp which entirely occludes the lumen of the aorta. The endoaortic partitioning device, on the other hand, provides a lumen for convenient introduction of the valvuloplasty catheter while the ascending aorta is occluded so that the valvuloplasty can be performed in conjunction with coronary artery bypass or another cardiac surgical procedure. Another advantage of combining the valvuloplasty catheter with the endoaortic partitioning device and cardiopulmonary bypass is that it will be easier to position the dilatation balloon across the aortic or mitral valve while the heart is still and with no blood flow through the heart that would make catheter placement difficult.

Other forms of heart valve repair can also be performed using the system for performing endovascular procedures of the present invention. Such procedures include heart valve debridement or decalcification, commissurotomy, annuloplasty, quadratic ressection, reattachment or shortening of the chordae tendineae or the papillary muscles. Specific examples of valvuloplasty catheters and other catheters and devices for heart valve repair suitable for use with the system for performing endovascular procedures of the present invention are described in the following patents, the entire disclosures of which are hereby incorporated by reference: U.S. Pat. No. 4,787,388 granted to Eugen Hofmann, U.S. Pat. No. 4,796,629 granted to Joseph Grayzel, U.S. Pat. No. 4,909,252 granted to Jeffrey Goldberger, and U.S. Pat. No. 5,295,958 granted to Leonid Shturman. Similarly to repair of defects in the heart valves of a patient, the system for performing endovascular procedures of the present invention can be used for performing repair of septal defects between two chambers of the heart, such as atrial septal defects or ventricular septal defects. Specific examples of catheter devices for repair of septal defects suitable for use with the system for performing endovascular procedures are described in the following patents, the entire disclosures of which are hereby incorporated by reference: U.S. Pat. No. 3,874,388 granted to King et al., and U.S. Pat. No. 4,874,089 granted to Sideris.

Figure 9B:
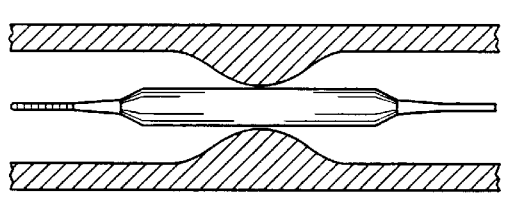
FIG. 9B is a close-up view of the deflated angioplasty balloon catheter crossing a stenosis within a coronary artery.
Figure 9C:
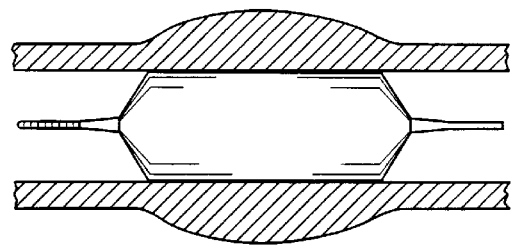
FIG. 9C is a close-up view of the angioplasty balloon catheter inflated within the stenosis.
Figure 9A:
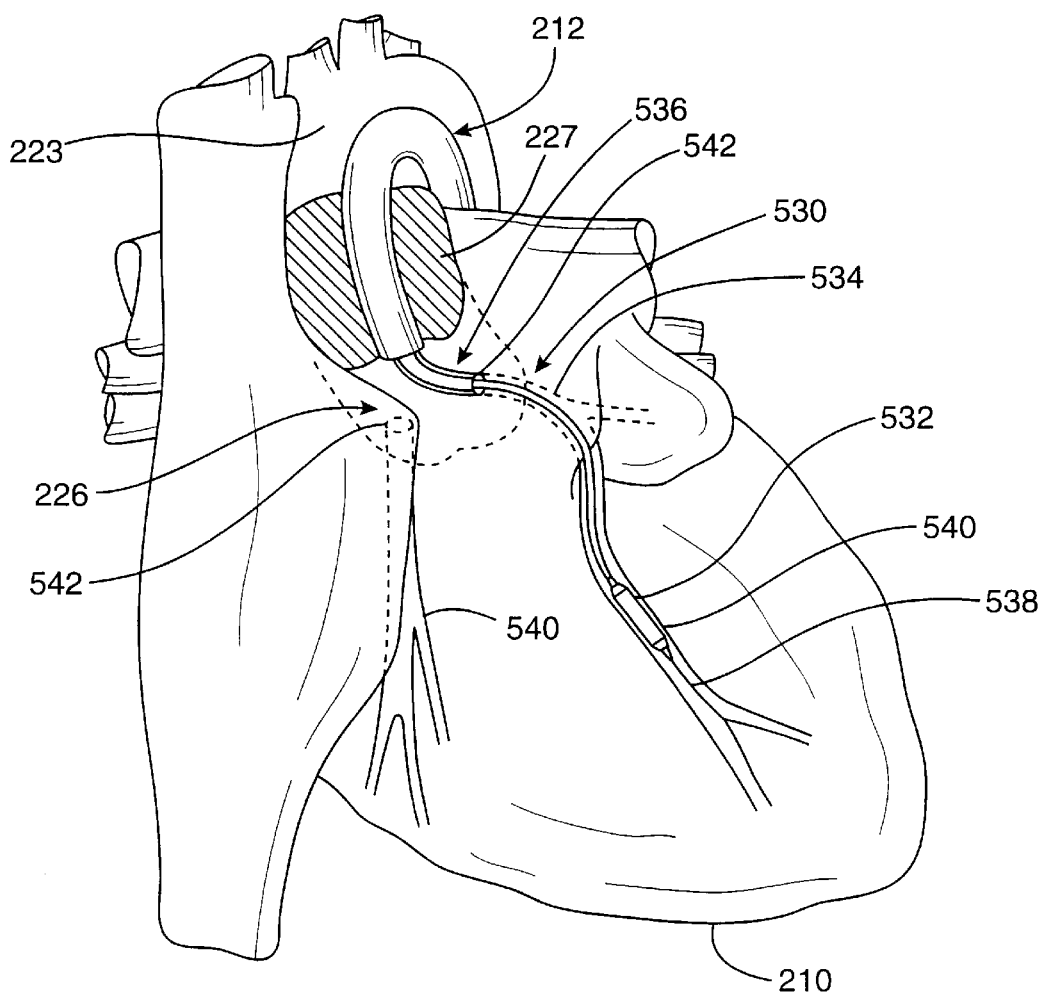
FIG. 9A is a view of a patient's heart with the endoaortic partitioning device placed in the ascending aorta and with an angioplasty balloon catheter inflated within a coronary artery.

FIGS. 9A, 9B and 9C show an embodiment of the system for performing endovascular procedures of the present invention that combines a coronary angioplasty system with the endoaortic partitioning device previously described. FIG. 9A shows a schematic representation of the patient's heart 210 and coronary arteries 540. The endoaortic partitioning device 212 has been percutaneously introduced into the ascending aorta 223 and the occlusion balloon 227 inflated to occlude the aortic lumen and to separate the heart 210 and the aortic root 226 from the remainder of the circulatory system. A coronary guiding catheter 536 is introduced through an internal lumen of the endoaortic partitioning device 212. The coronary guiding catheter 536 has a curved distal end which is configured to selectively engage one of the coronary ostia 542. Alternatively, the function of the coronary guiding catheter 536 may be incorporated into the endoaortic partitioning device 212 by providing it with a curved distal end configured to engage one of the coronary ostia 542. In this alternative embodiment, one or more infusion ports may be provided in the curved distal end of the endoaortic partitioning device 212, distal to the occlusion balloon 227, to distribute cardioplegic fluid delivered through the endoaortic partitioning device 212 to both coronary arteries. A coronary angioplasty catheter 530 is advanced through an internal lumen of the coronary guiding catheter 536 into the coronary artery 540. The coronary angioplasty catheter 530 has an expandable dilatation balloon 532 on the distal end of an elongated shaft 534. A fluid-filled syringe or other inflation device is attached to a fitting (not shown) on the proximal end of the shaft 534, similar to the system shown in FIG. 1. An inflation lumen within the shaft 534 connects the fitting with the interior of the dilatation balloon 532. A steerable coronary guidewire 538 may be used to selectively advance the coronary angioplasty catheter 530 through the coronary artery 540 under fluoroscopic guidance to the site of a coronary stenosis 544. The dilatation balloon 532 is advance across the stenosis 544 in a deflated state, as shown in FIG. 9B. The dilatation balloon 532 is inflated to dilate and expand the stenosis 544, as shown in FIG. 9C. When satisfactory results are achieved, the dilatation balloon 532 is deflated and the coronary angioplasty catheter 530 is withdrawn from the coronary artery 540.

Specific examples of coronary angioplasty catheters and guidewires suitable for use with the system for performing endovascular procedures of the present invention are described in the following patents, the entire disclosures of which are hereby incorporated by reference: U.S. Pat. No. 4,195,637, granted to Andreas Grüntzig and Hans Gleichner, U.S. Pat. No. 4,323,071 granted to John B. Simpson and Edward W. Robert, U.S. Pat. No. 4,545,390 granted to James J. Leary, U.S. Pat. No. 4,538,622 granted to Wilfred J. Samson and Ronald G. Williams, U.S. Pat. No. 4,616,653, granted to Wilfred J. Samson and Jeffrey S. Frisbie, U.S. Pat. No. 4,762,129, granted to Tassilo Bonzel, U.S. Pat. No. 4,988,356, granted to James F. Crittenden, U.S. Pat. No. 4,748,982 granted to Michael J. Horzewski and Paul G. Yock, and U.S. Pat. Nos. 5,040,548 and 5,061,273 granted to Paul G. Yock.

Figure 10B:
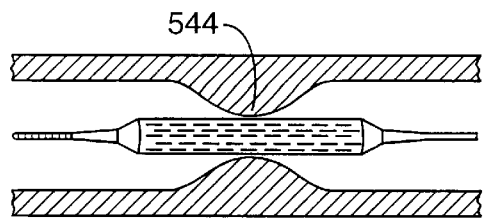
FIG. 10B is a close-up view of the stent delivery catheter with the balloon deflated crossing a stenosis within a coronary artery.
Figure 10C:
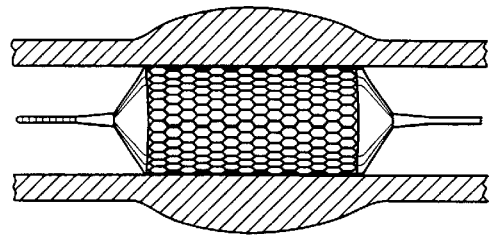
FIG. 10C is a close-up view of the stent delivery catheter with the balloon inflated to expand the stent within the stenosis.
Figure 10D:
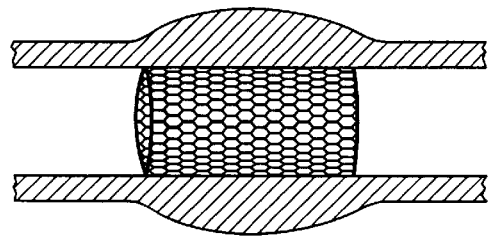
FIG. 10D is a close-up view of the coronary artery with the stent implanted across the stenosis.
Figure 10A:
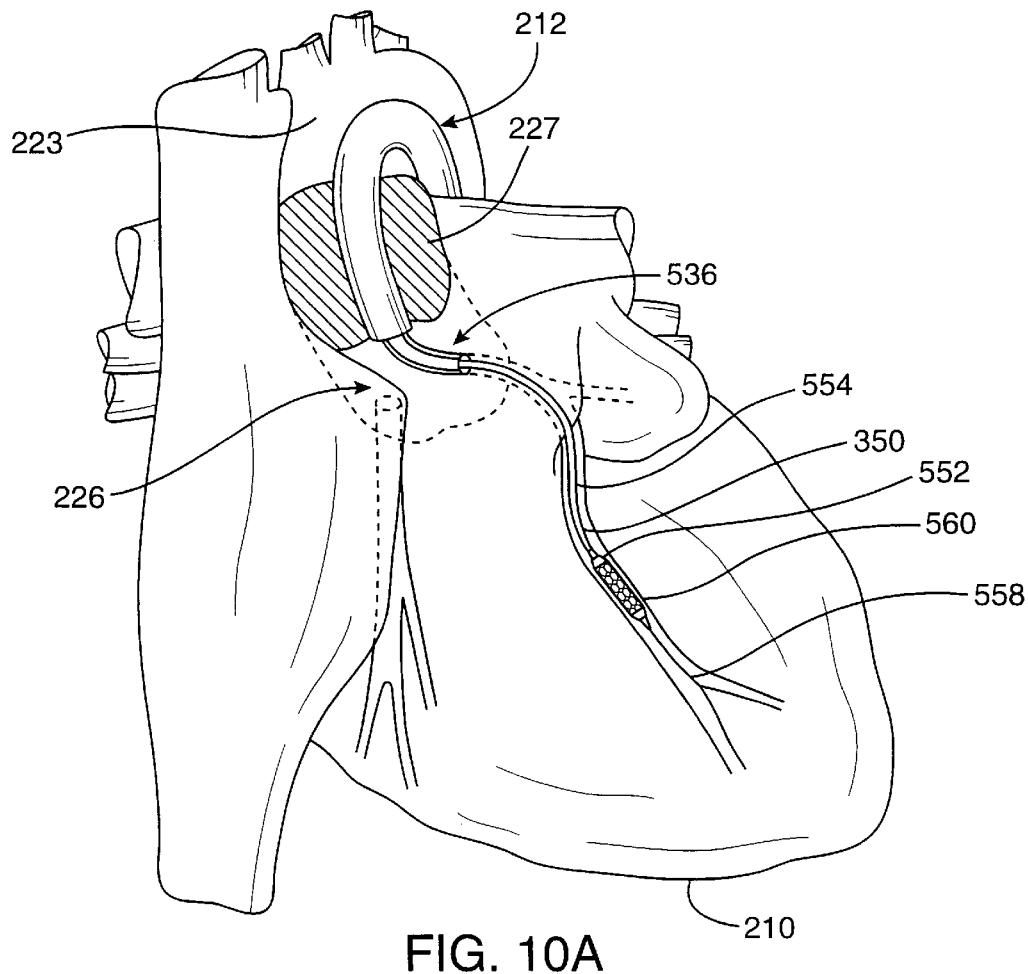
FIG. 10A is a view of a patient's heart with the endoaortic partitioning device placed in the ascending aorta and with a stent delivery catheter placed within a coronary artery.

FIGS. 10A, 10B, 10C and 10D show an embodiment of the system for performing endovascular procedures of the present invention that combines a coronary artery stent delivery system with the endoaortic partitioning device. FIG. 10A shows a schematic representation of the patient's heart 210 and coronary arteries 540. The endoaortic partitioning device 212 has been percutaneously introduced into the ascending aorta 223 and the occlusion balloon 227 inflated to occlude the aortic lumen and to separate the heart 210 and the aortic root 226 from the remainder of the circulatory system. A coronary guiding catheter 536, similar to that described in connection with FIG. 9A, is introduced through an internal lumen of the endoaortic partitioning device 212 and the curved distal end of the catheter selectively engages one of the coronary ostia 542. A stent delivery catheter 350, having a coronary artery stent 560 mounted thereon, is advanced through an internal lumen of the coronary guiding catheter 536 into the coronary artery 540.

The stent delivery catheter 350 has an expandable high pressure balloon 552 on the distal end of an elongated shaft 554. The coronary artery stent 560 is mounted, in a compressed state, over the expandable high pressure balloon 552. A fluid-filled syringe or other inflation device is attached to a fitting (not shown) on the proximal end of the shaft 554, similar to the system shown in FIG. 1. An inflation lumen within the shaft 554 connects the fitting with the interior of the expandable high pressure balloon 552. A steerable coronary guidewire 558 may be used to selectively advance the stent delivery catheter 350 through the coronary artery 540 under fluoroscopic guidance to the site of a coronary stenosis 544. The expandable high pressure balloon 552 in a deflated state with the compressed coronary artery stent 560 mounted thereon is advanced across the stenosis 544, as shown in FIG. 10B. The expandable high pressure balloon 552 is inflated to dilate the stenosis 544 and expand the coronary artery stent 560, as shown in FIG. 10C. The expandable high pressure balloon 552 is then deflated and the stent delivery catheter 350 is withdrawn, leaving the expanded coronary artery stent 560 within the coronary artery 540.

Examples of high pressure balloons suitable for expanding a coronary artery stent are described in the following patents, the entire disclosures of which are hereby incorporated by reference: U.S. Pat. No. 5,055,024, which describes the manufacture of polyamide balloons, and U.S. Pat. No. 4,490,421, which describes the manufacture of polyethylene terephthalate balloons. Examples of arterial stents and stent delivery catheters suitable for use with the system for performing endovascular procedures of the present invention are described in the following patents, the entire disclosures of which are hereby incorporated by reference: U.S. Pat. No. 5,041,126 granted to Cesare Gianturco, and U.S. Pat. Nos. 4,856,516 and 5,037,392 granted to Richard A. Hillstead.

The combination of coronary artery dilatation or dilatation plus stenting with the endoaortic partitioning device allows the patient's heart to be stopped and the circulatory system supported on cardiopulmonary bypass during the angioplasty procedure. Again, this may be useful for patients whose cardiac function is highly compromised so that they might not otherwise be good candidates for the procedure and for combining coronary angioplasty or stenting with other cardiac surgery procedures, such as coronary artery bypass grafting or heart valve repair or replacement.

Figure 11B:
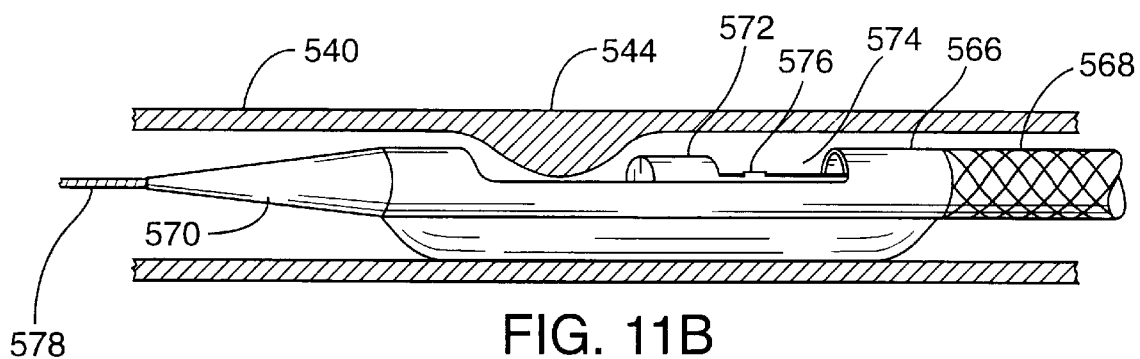
FIG. 11B is a close-up view of the atherectomy catheter removing atheroma from within a stenosis in a coronary artery.
Figure 11A:
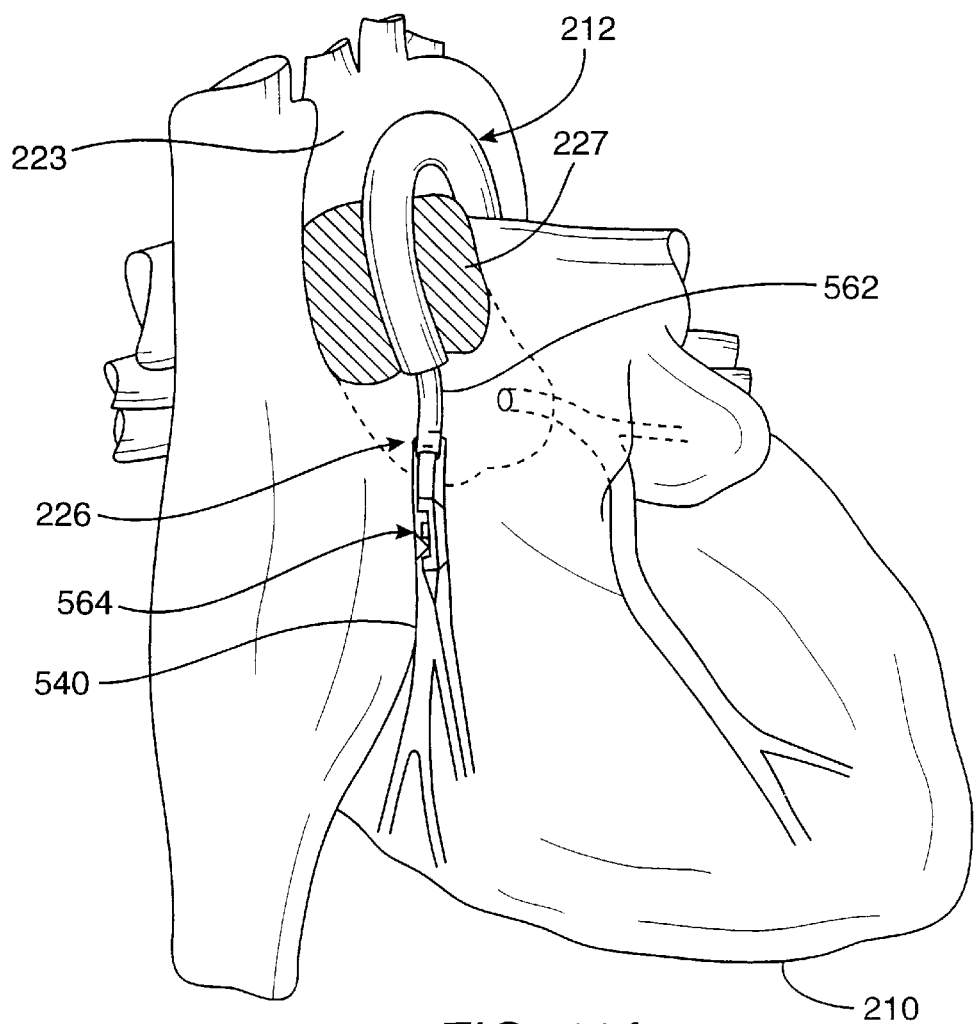
FIG. 11A is a view of a patient's heart with the endoaortic partitioning device placed in the ascending aorta and with an atherectomy catheter placed within a coronary artery.

FIGS. 11A and 11B show an embodiment of the system for performing endovascular procedures of the present invention that combines a coronary atherectomy system with the endoaortic partitioning device previously described.

FIG. 11A shows a schematic representation of the patient's heart 210 and coronary arteries 540. The endoaortic partitioning device 212 has been percutaneously introduced into the ascending aorta 223 and the occlusion balloon 227 inflated to occlude the aortic lumen and to separate the heart 210 and the aortic root 226 from the remainder of the circulatory system. An atherectomy guiding catheter 562 is introduced through an internal lumen of the endoaortic partitioning device 212. The atherectomy guiding catheter 562 has a curved distal end which is configured to selectively engage one of the coronary ostia 542.

A coronary atherectomy catheter, represented in this illustrative example by a directional coronary atherectomy catheter 564, is advanced through an internal lumen of the atherectomy guiding catheter 562 into the coronary artery 540. The directional coronary atherectomy catheter 564, shown in detail in FIG. 11B, has a tubular housing 566 mounted on the distal end of an elongated shaft 568. A rotary cutter 572 within the tubular housing 566 is exposed through a window 574 in the side of the housing 566. The rotary cutter 572 is driven by a flexible rotary driveshaft 576 that extends through the elongated shaft 568. A flexible, tapered distal end 570 extends from the distal end of the tubular housing 566. A guidewire passage for slidably receiving a steerable coronary guidewire 578 extends through the flexible rotary driveshaft 576, the rotary cutter 572 and out through the flexible, tapered distal end 570 of the atherectomy catheter 564. An expandable balloon is mounted on the side of the tubular housing 566 opposite to the window 574. A fluid-filled syringe or other inflation device is attached to a fitting (not shown) on the proximal end of the shaft 568. An inflation lumen within the shaft 568 connects the fitting with the interior of the expandable balloon.

In operation the directional coronary atherectomy catheter 564 is selectively advanced through the coronary artery 540 under fluoroscopic guidance to the site of a coronary stenosis 544. The tubular housing 566 is advanced across the stenosis 544, and the window 574 in the side of the housing is aligned with the stenosis 544. The expandable balloon is inflated to bias the rotary cutter 572 within the tubular housing 566 against the stenosis 544, as shown in FIG. 11B. The rotary cutter 572 is rotated by a motor drive unit (not shown) coupled to the proximal end of the flexible rotary driveshaft 576 and advanced distally to remove atheroma from within the stenosis 544. After enough of atheromatous material has been removed from the stenosis 544 to establish sufficient blood flow in the coronary artery 540, the expandable balloon is deflated and the directional coronary atherectomy catheter 564 is withdrawn from the coronary artery 540.

The combination of coronary atherectomy with the endoaortic partitioning device allows the patient's heart to be stopped and the circulatory system supported on cardiopulmonary bypass during the atherectomy procedure. As in the previous examples, this may be useful for patients whose cardiac function is highly compromised so that they might not otherwise be good candidates for the procedure and for combining coronary atherectomy with other cardiac surgery procedures, such as coronary artery bypass grafting or heart valve repair or replacement. The endovascular procedure system of the present invention is not limited to the illustrative example of directional coronary atherectomy, but may be useful with other endovascular devices for the removal of atheroma by atherectomy or endarterectomy. Examples of coronary atherectomy and endarterectomy catheters suitable for use with the system of the present invention are described in the following patents, the entire disclosures of which are hereby incorporated by reference: U.S. Pat. No. 4,323,071 granted to John B. Simpson and Kenneth A. Stenstrom, U.S. Pat. No. 5,071,425 granted to Hanson S. Gifford, III and Richard L. Mueller, U.S. Pat. No. 4,781,186 granted to John B. Simpson, Hanson S. Gifford, III, Hira Thapliyal and Tommy G. Davis, U.S. Pat. No. Re. 33,569 granted to Hanson S. Gifford, III and John B. Simpson, U.S. Pat. Nos. 4,290,427, 4,315,511 and 4,574,781 granted to Albert A. Chin, U.S. Pat. No. 4,621,636 granted to Thomas J. Fogarty, U.S. Pat. No. 4,890,611 granted to Michelle S. Monfort, Albert A. Chin and Kenneth H. Mollenauer, U.S. Pat. No. 5,368,603 granted to Alexander G. Halliburton, U.S. Pat. No. 3,730,183 granted to William A. Cook and Everett R. Lerwick, U.S. Pat. Nos. 5,071,424, 5,156,610 and 5,282,484 granted to Vincent A. Reger, U.S. Pat. No. 5,211,651 granted to Vincent A. Reger and Thomas L. Kelly, U.S. Pat. No. 5,267,955 granted to Donald W. Hanson, U.S. Pat. No. 5,195,956 granted to Uwe Stockmeier, U.S. Pat. No. 5,178,625 granted to LeRoy L. Groshong, U.S. Pat. No. 4,589,412 granted to Kenneth R. Kensey, U.S. Pat. No. 4,854,325 granted to Robert C. Stevens, U.S. Pat. No. 4,883,460 granted to Paul H. Zanetti, and U.S. Pat. No. 4,273,128 granted to Banning L. Lari.

Figure 12B:
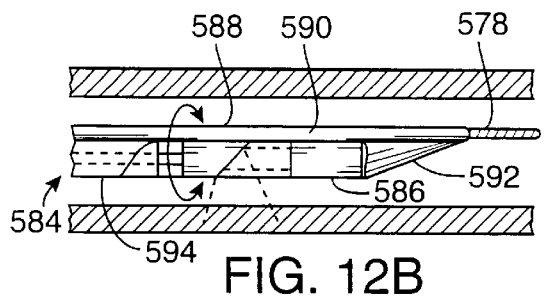
FIG. 12B is a close-up view of a first embodiment of the ultrasonic imaging catheter within a coronary artery.
Figure 12C:
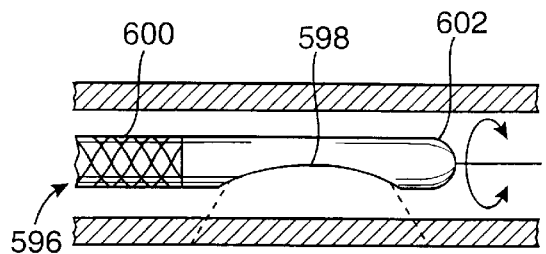
FIG. 12C is a close-up view of a second embodiment of the ultrasonic imaging catheter within a coronary artery.
Figure 12D:
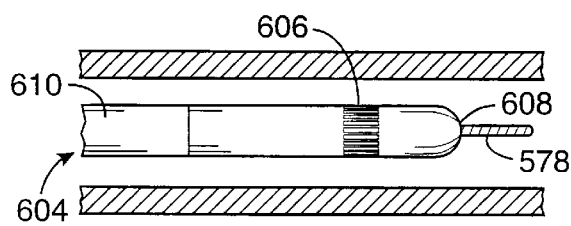
FIG. 12D is a close-up view of a phased array ultrasonic imaging catheter within a coronary artery.
Figure 12E:
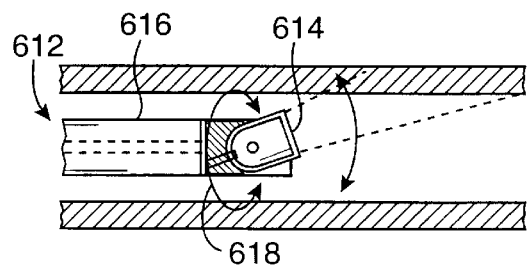
FIG. 12E is a close-up view of a forward viewing ultrasonic imaging catheter within a coronary artery.
Figure 12A:
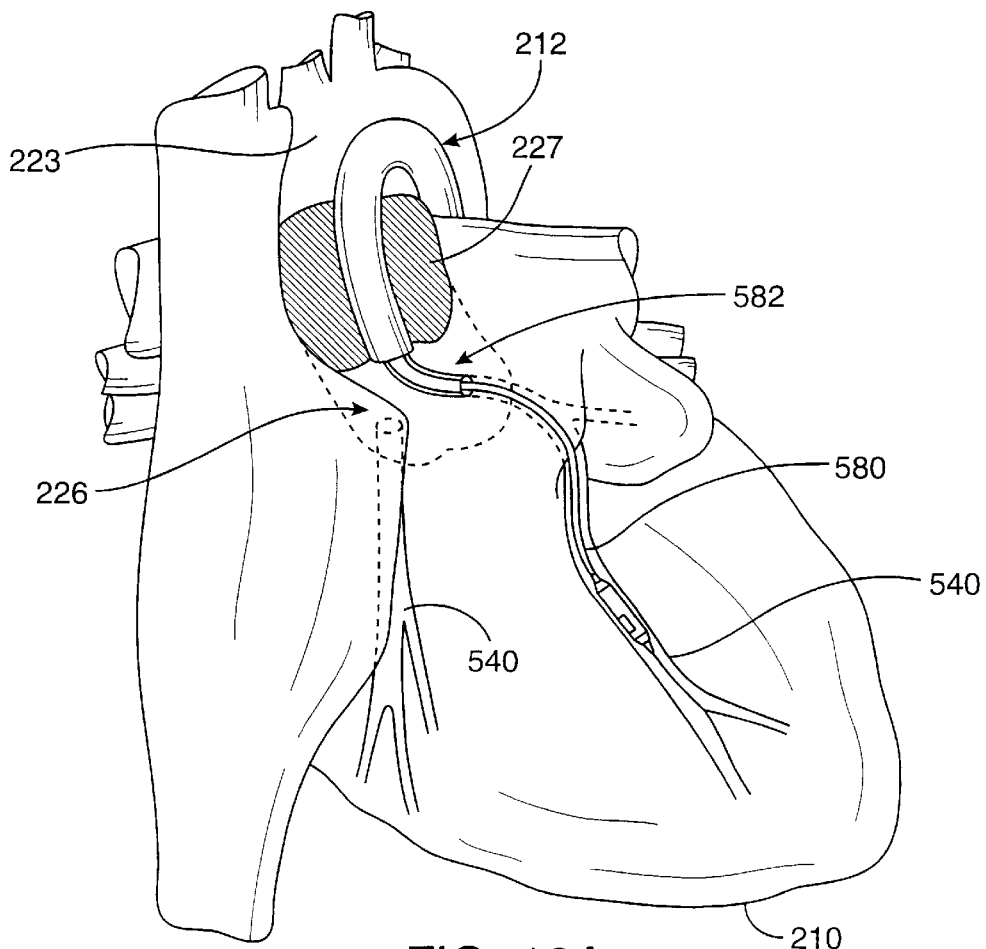
FIG. 12A is a view of a patient's heart with the endoaortic partitioning device placed in the ascending aorta and with an ultrasonic imaging catheter placed within a coronary artery.

FIGS. 12A, 12B, 12C, 12D and 12E show embodiments of the system for performing endovascular procedures of the present invention that combine an intravascular ultrasonic imaging system with the endoaortic partitioning device. FIG. 12A shows a schematic representation of the patient's heart 210 and coronary arteries 540. The endoaortic partitioning device 212 has been percutaneously introduced into the ascending aorta 223 and the occlusion balloon 227 inflated to occlude the aortic lumen and to separate the heart 210 and the aortic root 226 from the remainder of the circulatory system. An intravascular ultrasonic imaging catheter 580 is introduced through an internal lumen of the endoaortic partitioning device 212 and into a chamber or blood vessel of the patient's heart 210. The intravascular ultrasonic imaging catheter 580 can be used for visualizing and diagnosing stenosis, insufficiency or calcification of the aortic or mitral valves of the heart, calcification or coarctation of the aorta or other anomalous conditions of the patient's heart or great vessels. Optionally, a coronary guiding catheter 582 with a curved distal end may be used to direct the intravascular ultrasonic imaging catheter 580 toward one of the coronary ostia 542 and into a coronary artery 540. Within the coronary arteries 540, the intravascular ultrasonic imaging catheter 580 can be used for visualizing and diagnosing coronary artery disease.

FIG. 12B shows a first embodiment of an intravascular ultrasonic imaging catheter 584 suitable for use with the present system for performing endovascular procedures. The intravascular ultrasonic imaging catheter 584 has a piezoelectric transducer 586 which is mounted in the distal end of the catheter shaft 594 facing proximally. The piezoelectric transducer 586 is activated to produce pulses of ultrasonic energy. An angled reflective, rotating, ultrasonic mirror 588 directs the ultrasonic pulses from the piezoelectric transducer 586 radially outward from the catheter 584 to create an ultrasonic beam that sweeps in a 360° path around the catheter. The ultrasonic pulses are reflected off of structures in the tissue surrounding the ultrasonic imaging catheter 584. The reflected echoes strike the rotating mirror 588 and are directed back toward the piezoelectric transducer 586 which converts the received ultrasonic reflections to electrical signals. The electrical signals from the piezoelectric transducer 586 are sent to an ultrasound imaging unit (not shown) which creates an image of the tissue surrounding the ultrasonic imaging catheter 584. In a preferred embodiment of the ultrasonic imaging catheter 584, a guidewire passage 590 for slidably receiving a steerable coronary guidewire 578 extends alongside the rotating mirror 588 and the piezoelectric transducer 586 and out through a flexible, tapered distal end 592 on the catheter 584. The guidewire passage 590 may extend the full length of the catheter shaft 594, or it may extend along only a distal portion of the catheter shaft 594, to create a rapid exchange or monorail-type ultrasonic imaging catheter 584.

FIG. 12C shows a second embodiment of an intravascular ultrasonic imaging catheter 596 suitable for use with the present system for performing endovascular procedures. The intravascular ultrasonic imaging catheter 596 has a focused piezoelectric transducer 598 which is mounted on the distal end of a flexible drive shaft 600 facing radially outward. The piezoelectric transducer 598 and the flexible drive shaft 600 are surrounded by a protective sonolucent sheath 602. The piezoelectric transducer 598 is activated to produce pulses of ultrasonic energy as the flexible drive shaft 600 rotates to create an ultrasonic beam that sweeps in a 360° path around the catheter. The ultrasonic pulses are reflected off of structures in the tissue surrounding the ultrasonic imaging catheter 596. The reflected echoes strike the rotating mirror 588 and are directed back toward the piezoelectric transducer 598 which converts the received ultrasonic reflections to electrical signals. The electrical signals from the piezoelectric transducer 598 are sent to an ultrasound imaging unit (not shown) which creates an image of the tissue surrounding the ultrasonic imaging catheter 596.

FIG. 12D shows a third embodiment of an intravascular ultrasonic imaging catheter 604 suitable for use with the present system for performing endovascular procedures. The intravascular ultrasonic imaging catheter 604 has an annular array of piezoelectric transducers 606 arranged on the distal end of an elongated catheter shaft 610. Typically, the array of piezoelectric transducers 606 is made up of 32–64 individual transducer elements formed of a piezoelectric polymer, such as polyvinylidene fluoride. A guidewire passage 608 for slidably receiving a steerable coronary guidewire 578 extends through the elongated catheter shaft 610. The piezoelectric transducer array 606 is activated to produce pulses of ultrasonic energy to create an ultrasonic beam that radiates outward from the catheter. The piezoelectric transducer array 606 can be operated as if it was a single transducer by activating the transducer elements simultaneously or it can be operated as a phased array by activating the transducer elements sequentially to steer the ultrasonic beam. The ultrasonic pulses are reflected off of structures in the tissue surrounding the ultrasonic imaging catheter 604. The reflected echoes strike the piezoelectric transducer array 606 which converts the received ultrasonic reflections to electrical signals. The electrical signals from the piezoelectric transducer array 606 are sent to an ultrasound imaging unit (not shown) which creates an image of the tissue surrounding the ultrasonic imaging catheter 604.

FIG. 12E shows a fourth embodiment having a forward viewing intravascular ultrasonic imaging catheter 612 suitable for use with the present system for performing endovascular procedures. The forward viewing intravascular ultrasonic imaging catheter 612 has a piezoelectric transducer 614 pivotally mounted on the distal end of an elongated catheter shaft 616. A transducer drive mechanism 618 within the catheter 612 causes the piezoelectric transducer 614 to reciprocate back and forth in an arc. The piezoelectric transducer 614 is activated to produce pulses of ultrasonic energy as it reciprocates to create a sweeping ultrasonic beam directed distally from the catheter 612. The ultrasonic pulses are reflected off of structures in the tissue distal to the ultrasonic imaging catheter 612. The reflected echoes strike the piezoelectric transducer 614 which converts the received ultrasonic reflections to electrical signals. The electrical signals from the piezoelectric transducer 614 are sent to an ultrasound imaging unit (not shown) which creates an image of the tissue in front of the ultrasonic imaging catheter 612.

The combination of an intravascular ultrasonic imaging system with the endoaortic partitioning device allows the patient's heart and the blood vessels of the heart to be directly observed by ultrasonic imaging while the heart is stopped and the circulatory system is supported on cardiopulmonary bypass during the atherectomy procedure. This endovascular imaging prodedure may be performed as a primary diagnostic procedure or in preparation for or for observation during a therapeutic procedure such as repair or replacement of a heart valve or as an adjunct to a concomitant procedure on the heart. In addition, ultrasonic Doppler measurement or Doppler imaging of blood flow in the beating heart can be used to evaluate the efficacy of therapeutic procedures for coronary revascularization. Specific examples of intravascular ultrasonic imaging catheters and imaging systems suitable for use with the system for performing endovascular procedures of the present invention are described in the following patents, the entire disclosures of which are hereby incorporated by reference: U.S. Pat. Nos. 5,000,185 and 4,794,931 granted to Paul G. Yock, U.S. Pat. No. 5,029,588 granted to Paul G. Yock and James W. Arenson, U.S. Pat. No. 4,024,234 granted to James J. Leary and John R. McKenzie, U.S. Pat. No. 4,917,097 granted to Proudian et al., U.S. Pat. No. 5,167,233 granted to Eberle et al., U.S. Pat. No. 5,368,037 granted to Eberle et al., U.S. Pat. No. 5,190,046 granted to Leonid Shturman and published PCT application WO 94/16625 by John F. Maroney, William N. Aldrich and William M. Belef.

Figure 13B:
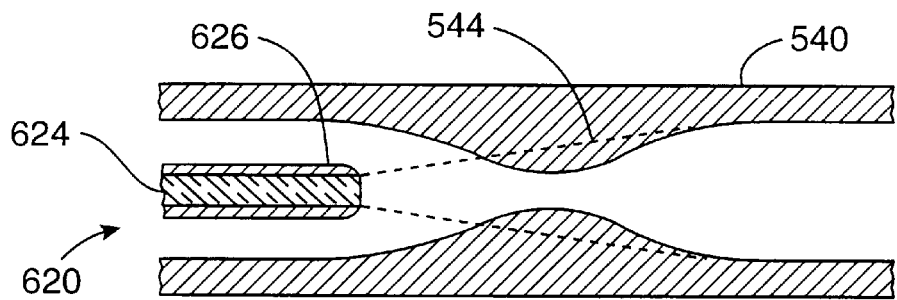
FIG. 13B is a close-up view of the laser angioplasty catheter ablating atheroma from within a stenosis in a coronary artery.
Figure 13A:
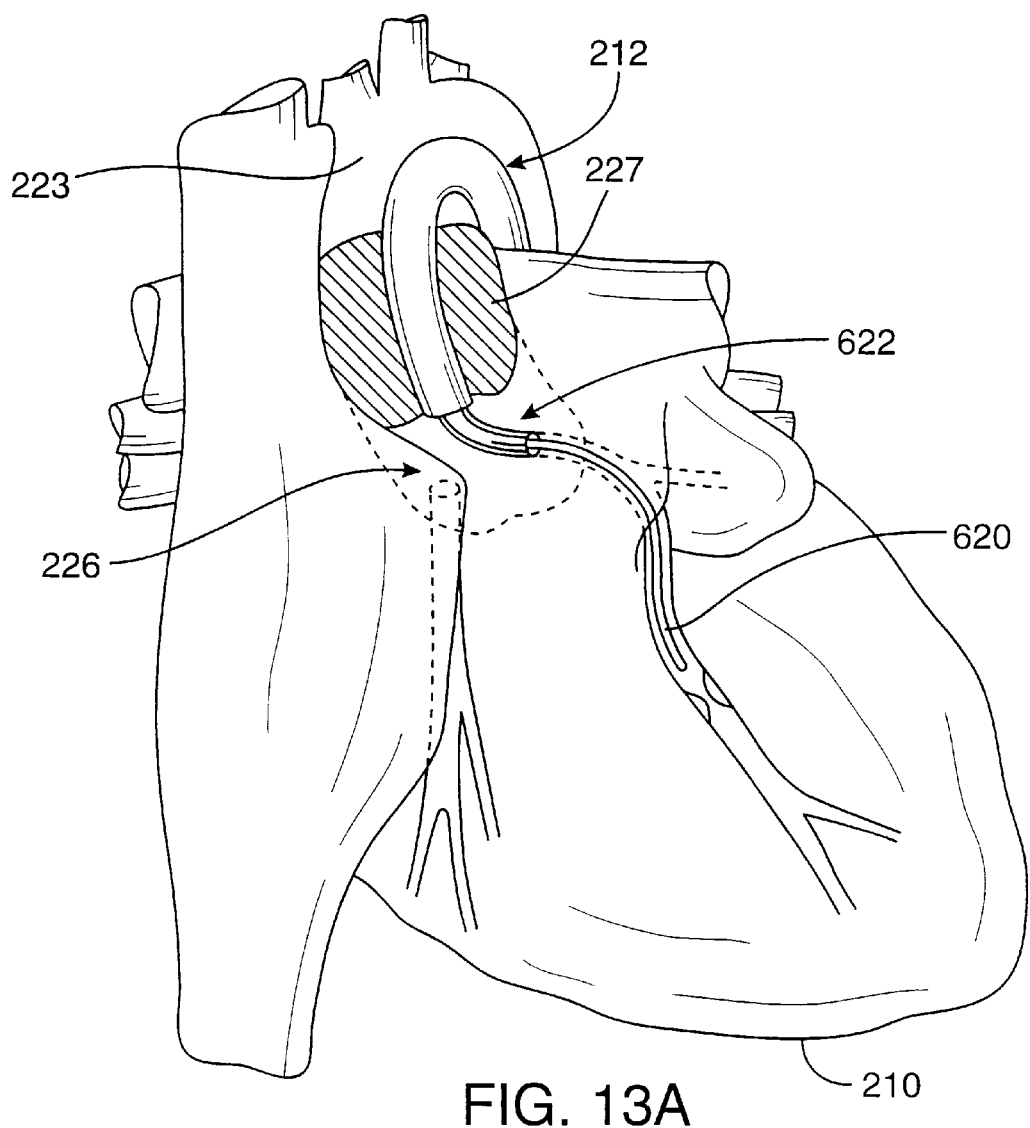
FIG. 13A is a view of a patient's heart with the endoaortic partitioning device placed in the ascending aorta and with a fiberoptic laser angioplasty catheter placed within a coronary artery.

FIGS. 13A and 13B show an embodiment of the system for performing endovascular procedures of the present invention that combines a laser angioplasty or ablation system with the endoaortic partitioning device previously described. The laser angioplasty or ablation system can be used for removal of atheroma from within a stenosis in the coronary arteries of the patient or for ablation of material within the heart or the blood vessels of the heart, such as ablation of scar tissue or calcification of a heart valve or ablation of an electrophysiological node within the heart walls. FIG. 13A shows a schematic representation of the patient's heart 210 and coronary arteries 540. The endoaortic partitioning device 212 has been percutaneously introduced into the ascending aorta 223 and the occlusion balloon 227 inflated to occlude the aortic lumen and to separate the heart 210 and the aortic root 226 from the remainder of the circulatory system which is supported on cardiopulmonary bypass. A laser angioplasty or ablation catheter 620 is introduced through an internal lumen of the endoaortic partitioning device 212. Optionally, a coronary guiding catheter 622 with a curved distal end may be used to direct the laser angioplasty catheter 620 toward one of the coronary ostia 542 and into a coronary artery 540.

FIG. 13B shows a close-up view of the laser angioplasty catheter 620 within a coronary artery 540. The laser angioplasty catheter 620 has an optical fiber 624 which extends the length of the catheter 620 and directs a beam of laser energy distally from the catheter tip 626. The laser energy irradiates and ablates the stenosis 544 within the coronary artery 540. Optional structures (not shown) can be added to the laser angioplasty catheter 620 to modify or direct the laser beam, such as a metal tip to convert a portion of the laser energy to heat, lenses to focus or diffuse the laser beam, and inflatable balloons or steering mechanisms to center the catheter tip within the vessel lumen or to direct the laser beam at a specific point in the heart or blood vessels.

Figure 14B:
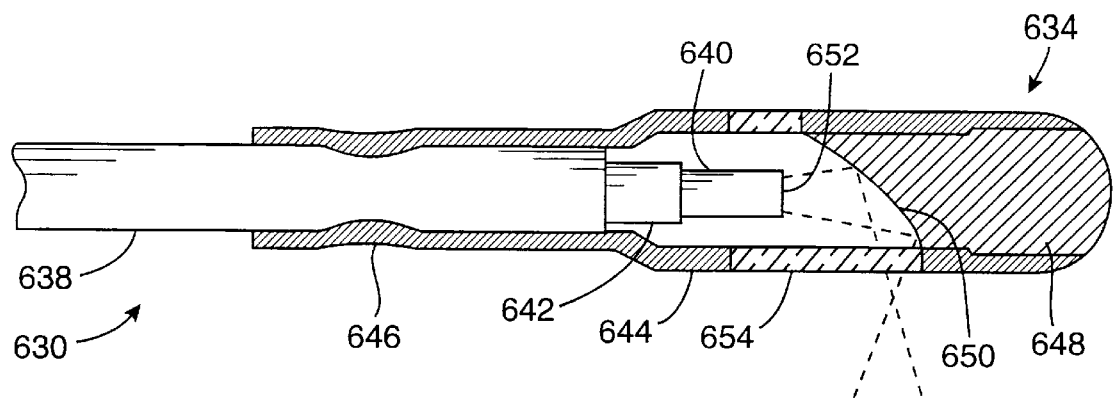
FIG. 14B is a cross section of tip of the side-firing fiberoptic laser catheter.
Figure 14A:
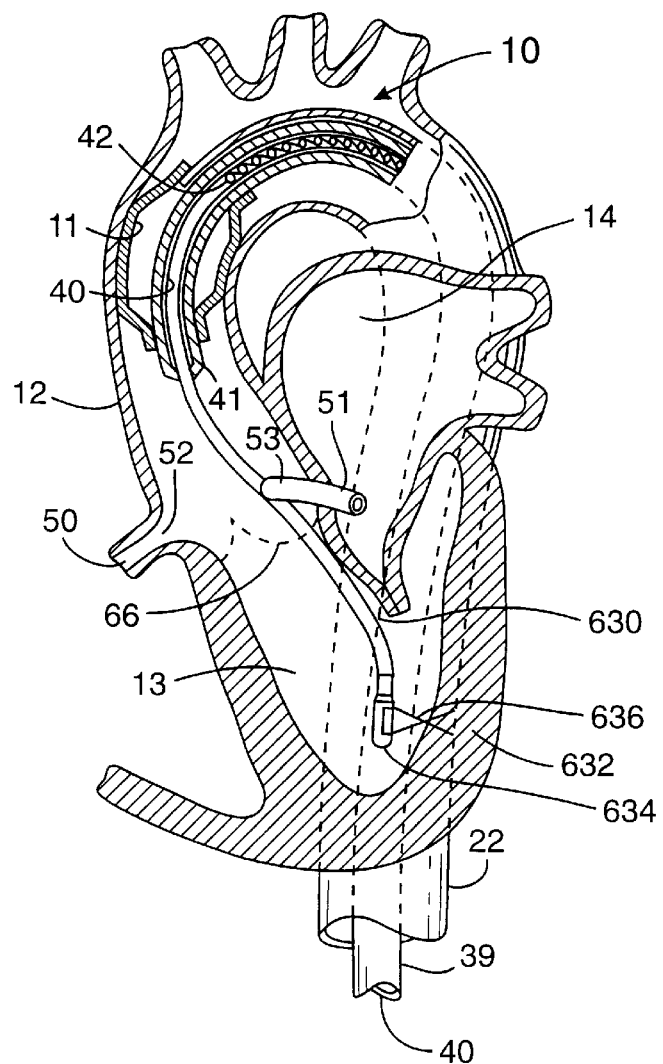
FIG. 14A is a view of a patient's heart with the endoaortic partitioning device placed in the ascending aorta and with a side-firing fiberoptic laser catheter performing transmyocardial revascularization from within the left ventricle of the heart.

FIGS. 14A and 14B show an embodiment of the system for performing endovascular procedures of the present invention that combines a side-firing fiberoptic laser catheter 630 with the endoaortic partitioning device previously described. The side-firing fiberoptic laser catheter can be used for performing transmyocardial revascularization from within the chambers of the heart or for ablation of material within the heart or the blood vessels of the heart, such as ablation of scar tissue or calcification of a heart valve or ablation of an electrophysiological node within the heart walls. FIG. 14A shows a schematic representation of the left side of a patient's heart cut away to show the interior of the left ventricle 13 and left atrium 14. The endoaortic partitioning device 10 has been percutaneously introduced into the ascending aorta 12 and the occlusion balloon 11 inflated to occlude the aortic lumen and to separate the heart and the aortic root from the remainder of the circulatory system which is supported on cardiopulmonary bypass. A side-firing fiberoptic laser catheter 630 is introduced through an internal lumen 40 of the endoaortic partitioning device 10. In FIG. 14A, the side-firing fiberoptic laser catheter 630 has been advanced through the aortic valve 66 and into the left ventricle 13 of the heart. The distal tip 634 of the catheter 630 has been positioned to direct a focused beam of laser energy 636 at the wall 632 of the left ventricle 13 to open a blood flow passage into the myocardium. In an alternate mode of operation, the side-firing fiberoptic laser catheter 630 can be introduced into one or more of the patient's coronary arteries and the laser beam 636 directed toward the left ventricle 13 to open a blood flow passage through the wall 632 from the ventricle 13 into the coronary artery.

FIG. 14B shows a cross section view of one possible embodiment of the distal tip 634 of the side-firing fiberoptic laser catheter 630. The catheter 630 has an elongated shaft 638 that contains an optical fiber 640 surrounded by a fiber cladding 642. A tubular metallic housing 644, which may be made of stainless steel, is attached to the elongated shaft 638 by suitable means such as a crimp 646. A reflective insert 648 is positioned within the tubular metallic housing 644. The reflective insert 648 has a highly reflective surface 650 which directs a laser beam emitted from the distal end 652 of the optical fiber 640 in a transverse direction so that it exits through an aperture 654 in the side of the housing 644. Preferably, the reflective surface 650 is highly reflective at the wavelength of the laser radiation to avoid undue heating of the catheter distal tip 634. A highly polished gold surface, provided by making the reflective insert 648 of gold or by plating a gold coating onto the reflective surface 650, can reflect up to 98% of the incident laser energy. The reflective surface 650 can be polished in a curve as shown so that the laser beam is focused at a selected distance from the catheter distal tip 634 to control the depth to which the blood flow passages are opened into the myocardium.

The combination of a side-firing fiberoptic laser catheter or other device for performing transmyocardial revascularization with the endoaortic partitioning device allows the patient's heart to be stopped and the circulatory system supported on cardiopulmonary bypass during the transmyocardial revascularization procedure. This will allow for more precise placement of the myocardial channels to achieve more complete or more effective revascularization. It also allows the combination of transmyocardial revascularization with other cardiac procedures that may be performed on the patient while the heart is stopped. The same holds true if the side-firing fiberoptic laser catheter is used for ablation of other material within the heart or the blood vessels of the heart or ablation of an electrophysiological node within the heart walls. With the endoaortic partitioning device 10 in place, the patient's heart can be stopped for precise localization and ablation of an electrophysiological node or path that is responsible for atrial or ventricular tachycardia or other electrophysiological problem of the heart. Then, the heart can be started again to see if the treatment has been effective by deflating the occlusion balloon 11 of the endoaortic partitioning device 10 and allowing warm blood to enter the coronary arteries and flush out the cardioplegic solution. The heart can thus be stopped and started repeatedly until satisfactory results have been achieved. Specific examples of laser angioplasty or ablation catheters and side-firing fiberoptic laser catheters suitable for use with the system for performing endovascular procedures of the present invention are described in the following patents, the entire disclosures of which are hereby incorporated by reference: U.S. Pat. No. 5,354,294 granted to Marilyn M. Chou, U.S. Pat. No. 5,366,456 granted to Rink et al., U.S. Pat. No. 5,163,935 granted to Michael Black, U.S. Pat. No. 4,740,047 granted to Abe et al., U.S. Pat. No. 5,242,438 granted to Saadatmanesh et al., U.S. Pat. No. 5,147,353 granted to Royice B. Everett, U.S. Pat. No. 5,242,437 granted to Everett et al., U.S. Pat. No. 5,188,634 granted to Hussein et al., U.S. Pat. No. 5,026,366 granted to Michael E. Leckrone, and U.S. Pat. No. 4,788,975 granted to Steven L. Jensen and Leonid Shturman.

Figure 15:
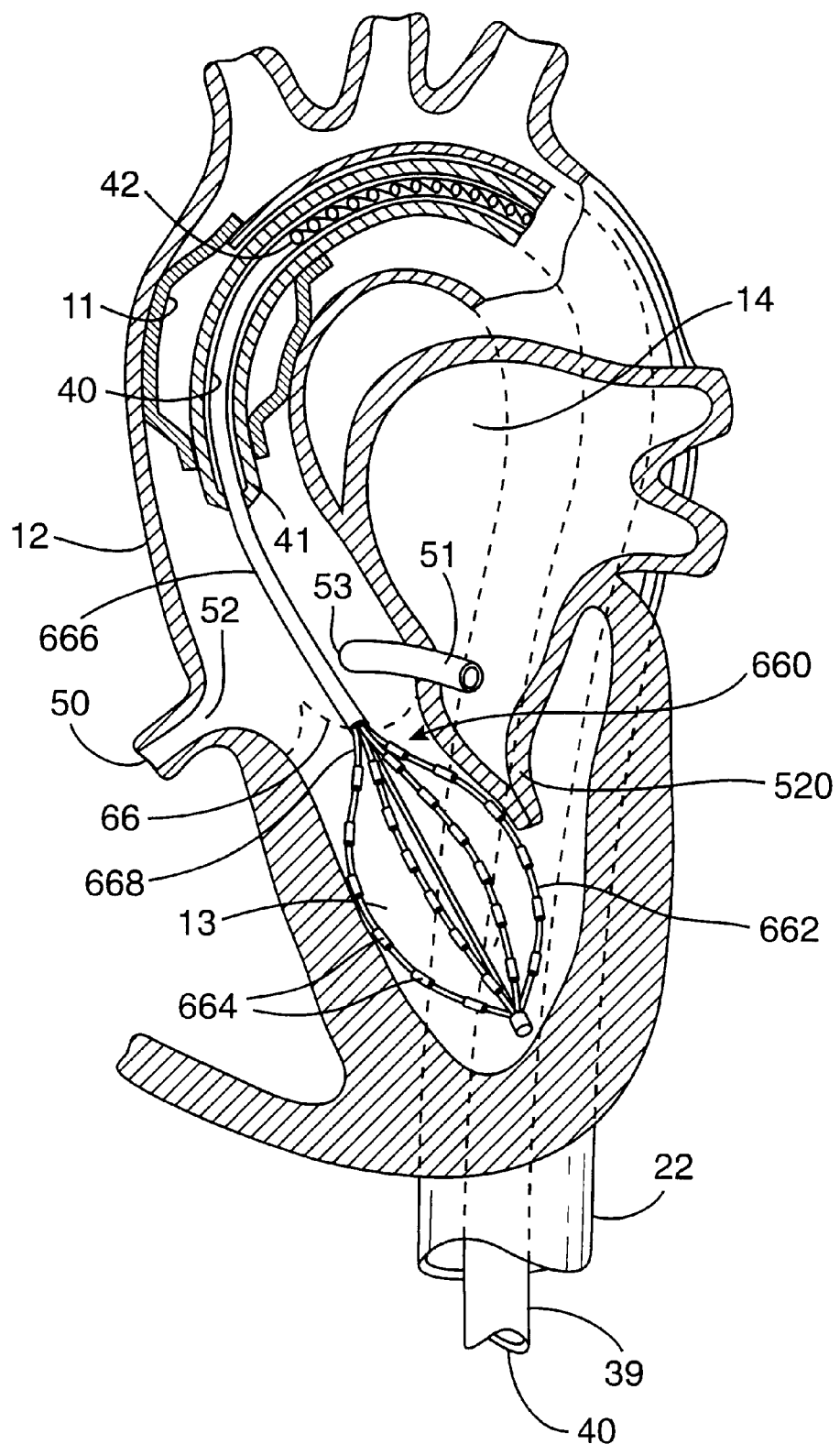
FIG. 15 is a view of a patient's heart with the endoaortic partitioning device placed in the ascending aorta and with an electrophysiology mapping and ablation catheter within the left ventricle of the heart.

FIG. 15 shows an exemplary embodiment of the system for performing endovascular procedures of the present invention that combines an electrophysiology mapping and ablation catheter 660 with the endoaortic partitioning device previously described. FIG. 15 shows a schematic representation of the left side of a patient's heart cut away to show the interior of the left ventricle 13 and left atrium 14. The endoaortic partitioning device 10 has been percutaneously introduced into the ascending aorta 12 and the occlusion balloon 11 may be inflated to occlude the aortic lumen and to separate the heart and the aortic root from the remainder of the circulatory system. A multi-electrode endocardial electrophysiology mapping and ablation catheter 660 is introduced through an internal lumen 40 of the endoaortic partitioning device 10. In FIG. 15 the electrophysiology catheter 660 has been advanced through the aortic valve 66 and into the left ventricle 13 of the heart.

The electrophysiology catheter 660 has four wire assemblies 662 that extend through an elongated catheter shaft 666. Each of the wire assemblies 662 has multiple electrodes 664, six per wire assembly in this illustrative example, which are each connected to separate insulated electrical wires (not shown) within the catheter shaft 666. Separate electrical connectors (not shown) are connected to each of the electrical wires on the proximal end of the catheter 660. The wire assemblies 662 are compressible so that they can be withdrawn into an internal lumen 668 within the catheter shaft 666 for introduction of the device 660 through the endoaortic partitioning device 10. When extended from the catheter shaft 666, the wire assemblies 662 expand within the left ventricle 13 of the heart to hold the electrodes 664 in electrical contact with the interior wall of the ventricle 13. The electrophysiology catheter 660 can likewise be advanced through the mitral valve 520 and expanded in the left atrium 14 of the heart.

The electrophysiology catheter 660 can be used to map the electrically conductive pathways in the ventricular wall and to locate any abnormal foci that could result in atrial or ventricular tachycardia or other electrophysiological problems of the heart. Once the abnormal foci have been localized they can be ablated by applying a direct or alternating current across the two closest adjoining electrodes to the site sufficient to permanently disrupt the flow of electrical impulses along that path. Alternatively, another ablation catheter may be used to localize and ablate the abnormal foci once they have been diagnosed. Specific examples of electrophysiology mapping and ablation catheters suitable for use with the system for performing endovascular procedures of the present invention are described in the following patents, the entire disclosures of which are hereby incorporated by reference: U.S. Pat. No. 4,699,147 granted to Donald A. Chilson and Kevin W. Smith, U.S. Pat. No. 5,327,889 granted to Mir A. Imran, U.S. Pat. No. 4,960,134 granted to Wilton W. Webster, U.S. Pat. No. 5,140,987 granted to Claudio Schuger and Russell T. Steinman, U.S. Pat. No. 4,522,212 granted to Sandra I. Gelinas, Daniel G. Cerundolo and john A. Abele, U.S. Pat. No. 4,660,571 granted to Stanley R. Hess and Terri Kovacs, U.S. Pat. No. 4,664,120 granted to Stanley R. Hess, U.S. Pat. No. 5,125,896 granted to Hikmat J. Hojeibane, and U.S. Pat. No. 5,104,393 granted to Jeffrey M. Isner and Richard Clarke.

In each of the above examples, the system for performing endovascular procedures of the present invention can be operated in a variety of different operating modes depending on the nature and circumstances of the endovascular procedure to be performed. In many cases it will be desirable to combine an endovascular procedure with another surgical procedure on the heart performed using either a thoracoscopic or a standard open chest approach. In these cases, either or both of the endovascular procedure and the surgical procedure may be performed while the patient's circulatory system is supported by a cardiopulmonary bypass system. Also, if desired, the endoaortic occlusion balloon of the endoaortic partitioning catheter may be inflated to isolate the patient's heart and a cardioplegic agent infused through the endoaortic partitioning catheter to stop the patient's heart while performing the endovascular procedure and/or the surgical procedure. In some cases it will be desirable to perform the endovascular procedure while the heart is still beating and to only stop the heart for all or a part of the surgical procedure, or vice versa, in order to reduce the overall clamp time. The endovascular procedure and the surgical procedure may be performed simultaneously or serially in either order. One example of this operating mode discussed above is the combination of angioplasty, atherectomy or endarterectomy with CABG surgery in order to realize a more complete revascularization of the patient's heart.

In other cases, one or more endovascular procedures may be performed on the patient's heart without combining them with another surgical procedure. This mode of operation will be advantageous when it is desirable to stop the heart to facilitate performing the endovascular procedure or to relieve the stress on the heart during a high risk interventional procedure. This may allow the application of various endovascular procedures to patients whose cardiac function is highly compromised and therefore might not otherwise be good candidates for the procedure.

In an alternate mode of operation the endoaortic partitioning catheter can be used as a guiding catheter for introducing an endovascular device and for performing an endovascular procedure while the patient is on partial cardiopulmonary support without inflating the occlusion balloon or inducing cardiac arrest. If and when it is desired, the endoaortic partitioning catheter can be activated to occlude the aorta and induce cardioplegia, thereby converting the patient from partial cardiopulmonary support to full cardiopulmonary bypass. This mode of operation would be advantageous when it was desired to follow the endovascular procedure with another surgical procedure on the heart using either a thoracoscopic or standard open chest approach. It would also be advantageous when performing a high risk interventional procedure so that, in the event of complications, the patient can be immediately placed on full cardiopulmonary bypass and prepared for emergency surgery without delay.

In each of these operating modes, the system for performing endovascular procedures built in accordance with the present invention provides a number of advantages heretofore unknown. Particularly, it allows a compatible combination of devices for performing endovascular procedures with the capability of performing complete cardioplumonary bypass and cardioplegic arrest for myocardial preservation. It also allows the combination of one or more endovascular procedures with surgical procedures on the heart or blood vessels in a manner that facilitates both types of procedures and reduces the invasiveness of the procedures, thereby reducing the trauma and morbidity to the patient as a result.

While the present invention has been described herein in terms of certain preferred embodiments, it will be apparent to one of ordinary skill in the art that many modifications and improvements can be made to the invention without departing from the scope thereof.

What is claimed is:

1. A method for performing an endovascular procedure on a patient, the method comprising steps of:
    a) placing an elongated aortic occlusion catheter at a location within the patient's ascending aorta, the aortic occlusion catheter having a proximal end, a distal end, and an expandable member, the expandable member of the aortic occlusion catheter being movable to an expanded shape which is sized and configured to substantially occlude a passageway in the patient's ascending aorta downstream of the ostia of the coronary arteries, the aortic occlusion catheter also including a lumen having an outlet;
    b) expanding the expandable member of the aortic occlusion catheter within the patient's ascending aorta to substantially completely occlude the passageway therein downstream of the ostia of the patient's coronary arteries and without occluding said ostia thereby blocking blood flow through the aorta;
    c) placing a coronary catheter having a proximal end, a distal end and an expandable member through the lumen of the aortic occlusion catheter until the distal end of the coronary catheter exits the lumen of the aortic occlusion catheter;
    d) directing the coronary catheter into one of the patient's coronary arteries; and
    e) expanding the expandable member of the coronary catheter within the patient's coronary artery.

* * * * *